US011773456B2

(12) United States Patent
Liu et al.

(10) Patent No.: US 11,773,456 B2
(45) Date of Patent: Oct. 3, 2023

(54) LOOP-MEDIATED ISOTHERMAL AMPLIFICATION (LAMP) PRIMER SETS FOR DETECTING PORCINE SUSCEPTIBILITY-RELATED PATHOGENIC BACTERIA, AND KIT, LAMP CHIP AND USE BASED ON THE SAME

(71) Applicant: Anhui Agricultural University, Hefei (CN)

(72) Inventors: Xuelan Liu, Hefei (CN); Yu Li, Hefei (CN); Jie Tang, Hefei (CN); Xiaohui Huang, Hefei (CN); Lin Li, Hefei (CN); Hong Ye, Hefei (CN); Yin Dai, Hefei (CN); Liang Li, Hefei (CN)

(73) Assignee: Anhui Agricultural University, Hefei (CN)

( * ) Notice: Subject to any disclaimer, the term of this patent is extended or adjusted under 35 U.S.C. 154(b) by 0 days.

(21) Appl. No.: 17/820,601

(22) Filed: Aug. 18, 2022

(65) Prior Publication Data

US 2023/0086107 A1 Mar. 23, 2023

(30) Foreign Application Priority Data

Aug. 23, 2021 (CN) ......................... 202110965791.1

(51) Int. Cl.
*C12Q 1/689* (2018.01)
*C12Q 1/6837* (2018.01)

(52) U.S. Cl.
CPC ........... *C12Q 1/689* (2013.01); *C12Q 1/6837* (2013.01); *C12Q 2600/16* (2013.01)

(58) Field of Classification Search
None
See application file for complete search history.

(56) References Cited

PUBLICATIONS

Yang (FEMS Microbiol Lett 300 (2009) 83-89).*
Chen (FEMS Immunol Med Microbiol 60 (2010) 283-285).*
Chen (Food Sciences and Human Wellness 4 (2015) pp. 75-79).*
Zang (Pesq Vet Bras 33 (10) 1222-1226 2013).*
Sun (Vet Res Commun (2010) 34:649-657).*
Arai (International Journal of Food Microbiology vol. 208 Sep. 2, 2015 pp. 35-42).*
Yamazaki (Letters in Applied Microbiology 58, 362-369 2013 pp. 362-369).*

* cited by examiner

*Primary Examiner* — Amanda Haney
(74) *Attorney, Agent, or Firm* — FRESH IP PLC; Andrew Berks

(57) ABSTRACT

The present disclosure belongs to the technical field of pathogen detection, in particular to loop-mediated isothermal amplification (LAMP) primer sets for detecting porcine susceptibility-related pathogenic bacteria, and a kit, a LAMP chip and use based on the same. The LAMP primer sets for detecting porcine susceptibility-related pathogenic bacteria include an *Actinobacillus pleuropneumoniae* primer set, a *Haemophilus parasuis* primer set, a *Salmonella choleraesuis* primer set, a *Bordetella bronchiseptica* primer set, a *Pasteurella multocida* primer set, a *Streptococcus suis* primer set, and an *Erysipelothrix rhusiopathiae* primer set.

8 Claims, 8 Drawing Sheets

Specification includes a Sequence Listing.

*Streptococcus suis*

*Erysipelothrix rhusiopathiae*

SEQUENCE LISTING

```
Sequence total quantity: 35
SEQ ID NO: 1           moltype = DNA  length = 19
FEATURE                Location/Qualifiers
source                 1..19
                       mol_type = other DNA
                       note = Forward outer primer for Actinobacillus
                        pleuropneumoniae
                       organism = synthetic construct
SEQUENCE: 1
cccttagccc cttacacta                                                19

SEQ ID NO: 2           moltype = DNA  length = 18
FEATURE                Location/Qualifiers
source                 1..18
                       mol_type = other DNA
                       note = Reverse outer primer for Actinobacillus
                        pleuropneumoniae
                       organism = synthetic construct
SEQUENCE: 2
cgcttaggat ccgcctta                                                 18

SEQ ID NO: 3           moltype = DNA  length = 40
FEATURE                Location/Qualifiers
source                 1..40
                       mol_type = other DNA
                       note = Forward inner primer for Actinobacillus
                        pleuropneumoniae
                       organism = synthetic construct
SEQUENCE: 3
caccaccgag aaacaaatcc tcggcgtggt ttatgtcacc                         40

SEQ ID NO: 4           moltype = DNA  length = 45
FEATURE                Location/Qualifiers
source                 1..45
                       mol_type = other DNA
                       note = Reverse inner primer for Actinobacillus
                        pleuropneumoniae
                       organism = synthetic construct
SEQUENCE: 4
aggcgataca attgaagacg ccggtacccc tttttctctc accac                   45

SEQ ID NO: 5           moltype = DNA  length = 18
FEATURE                Location/Qualifiers
source                 1..18
                       mol_type = other DNA
                       note = Forward outer primer for Haemophilus parasuis
                       organism = synthetic construct
SEQUENCE: 5
acctactttt acgcctcc                                                 18

SEQ ID NO: 6           moltype = DNA  length = 18
FEATURE                Location/Qualifiers
source                 1..18
                       mol_type = other DNA
                       note = Reverse outer primer for Haemophilus parasuis
                       organism = synthetic construct
SEQUENCE: 6
gcattggtca agctggtt                                                 18

SEQ ID NO: 7           moltype = DNA  length = 41
FEATURE                Location/Qualifiers
source                 1..41
                       mol_type = other DNA
                       note = Forward inner primer for Haemophilus parasuis
                       organism = synthetic construct
SEQUENCE: 7
caggcattga aggtttgacg tttatcatca cgctcatttg c                       41

SEQ ID NO: 8           moltype = DNA  length = 46
FEATURE                Location/Qualifiers
source                 1..46
                       mol_type = other DNA
```

-continued

```
                        note = Reverse inner primer for Haemophilus parasuis
                        organism = synthetic construct
SEQUENCE: 8
accttttttg tttgtgttgt ttgctaaagt ataggtgttg gtactg                    46

SEQ ID NO: 9            moltype = DNA  length = 23
FEATURE                 Location/Qualifiers
source                  1..23
                        mol_type = other DNA
                        note = Forward outer primer for Salmonella choleraesuis
                        organism = synthetic construct
SEQUENCE: 9
cattgccaag tatctgtatc agc                                             23

SEQ ID NO: 10           moltype = DNA  length = 20
FEATURE                 Location/Qualifiers
source                  1..20
                        mol_type = other DNA
                        note = Reverse outer primer for Salmonella choleraesuis
                        organism = synthetic construct
SEQUENCE: 10
ccggatgcac taaggcttta                                                 20

SEQ ID NO: 11           moltype = DNA  length = 41
FEATURE                 Location/Qualifiers
source                  1..41
                        mol_type = other DNA
                        note = Forward inner primer for Salmonella choleraesuis
                        organism = synthetic construct
SEQUENCE: 11
ggaaggatgc cattttgccc ggttagctcc ccattctgct c                         41

SEQ ID NO: 12           moltype = DNA  length = 38
FEATURE                 Location/Qualifiers
source                  1..38
                        mol_type = other DNA
                        note = Reverse inner primer for Salmonella choleraesuis
                        organism = synthetic construct
SEQUENCE: 12
tgagtgggct tgtcggtagt caacacacca aactctgc                             38

SEQ ID NO: 13           moltype = DNA  length = 19
FEATURE                 Location/Qualifiers
source                  1..19
                        mol_type = other DNA
                        note = Forward outer primer for Bordetella bronchiseptica
                        organism = synthetic construct
SEQUENCE: 13
tgacggtcga tcaatggtg                                                  19

SEQ ID NO: 14           moltype = DNA  length = 19
FEATURE                 Location/Qualifiers
source                  1..19
                        mol_type = other DNA
                        note = Reverse outer primer for Bordetella bronchiseptica
                        organism = synthetic construct
SEQUENCE: 14
agccagctgg aatcatgga                                                  19

SEQ ID NO: 15           moltype = DNA  length = 39
FEATURE                 Location/Qualifiers
source                  1..39
                        mol_type = other DNA
                        note = Forward inner primer for Bordetella bronchiseptica
                        organism = synthetic construct
SEQUENCE: 15
tcgattccac gcgcgatcag tcccctgcag aaagtacgg                            39

SEQ ID NO: 16           moltype = DNA  length = 42
FEATURE                 Location/Qualifiers
source                  1..42
                        mol_type = other DNA
                        note = Reverse inner primer for Bordetella bronchiseptica
                        organism = synthetic construct
SEQUENCE: 16
ggcattgaat attgcctggg gcaacatggt gaaaagaccc gg                        42
```

-continued

```
SEQ ID NO: 17          moltype = DNA  length = 18
FEATURE                Location/Qualifiers
source                 1..18
                       mol_type = other DNA
                       note = Forward outer primer for Pasteurella multocida
                       organism = synthetic construct
SEQUENCE: 17
cgttgtcaag gaagcaga                                            18

SEQ ID NO: 18          moltype = DNA  length = 18
FEATURE                Location/Qualifiers
source                 1..18
                       mol_type = other DNA
                       note = Reverse outer primer for Pasteurella multocida
                       organism = synthetic construct
SEQUENCE: 18
tccgctattt acccagtg                                            18

SEQ ID NO: 19          moltype = DNA  length = 43
FEATURE                Location/Qualifiers
source                 1..43
                       mol_type = other DNA
                       note = Forward inner primer for Pasteurella multocida
                       organism = synthetic construct
SEQUENCE: 19
cgagccataa aataatgcca tttccgtgcg aatgaaccga ttg                43

SEQ ID NO: 20          moltype = DNA  length = 38
FEATURE                Location/Qualifiers
source                 1..38
                       mol_type = other DNA
                       note = Reverse inner primer for Pasteurella multocida
                       organism = synthetic construct
SEQUENCE: 20
tgagtgggct tgtcggtagt caacacacca aactctgc                      38

SEQ ID NO: 21          moltype = DNA  length = 18
FEATURE                Location/Qualifiers
source                 1..18
                       mol_type = other DNA
                       note = Forward outer primer for Streptococcus suis
                       organism = synthetic construct
SEQUENCE: 21
acaccgatgt caccagca                                            18

SEQ ID NO: 22          moltype = DNA  length = 19
FEATURE                Location/Qualifiers
source                 1..19
                       mol_type = other DNA
                       note = Reverse outer primer for Streptococcus suis
                       organism = synthetic construct
SEQUENCE: 22
tcgcttccac ccaactgta                                           19

SEQ ID NO: 23          moltype = DNA  length = 40
FEATURE                Location/Qualifiers
source                 1..40
                       mol_type = other DNA
                       note = Forward inner primer for Streptococcus suis
                       organism = synthetic construct
SEQUENCE: 23
tgcgcttctg ccaaagcttc agacgtcaag tgaaggtccg                    40

SEQ ID NO: 24          moltype = DNA  length = 40
FEATURE                Location/Qualifiers
source                 1..40
                       mol_type = other DNA
                       note = Reverse inner primer for Streptococcus suis
                       organism = synthetic construct
SEQUENCE: 24
ccacctttac caccgccgat agttcctcgg ttttgagcaa                    40

SEQ ID NO: 25          moltype = DNA  length = 19
FEATURE                Location/Qualifiers
source                 1..19
                       mol_type = other DNA
                       note = Forward outer primer for Erysipelothrix rhusiopathia
                       organism = synthetic construct
```

-continued

```
SEQUENCE: 25
cggctcgaaa atatgatgg                                             19

SEQ ID NO: 26          moltype = DNA  length = 20
FEATURE                Location/Qualifiers
source                 1..20
                       mol_type = other DNA
                       note = Reverse outer primer for Erysipelothrix rhusiopathia
                       organism = synthetic construct
SEQUENCE: 26
gaacatctcc acttctttgg                                            20

SEQ ID NO: 27          moltype = DNA  length = 46
FEATURE                Location/Qualifiers
source                 1..46
                       mol_type = other DNA
                       note = Forward inner primer for Erysipelothrix rhusiopathiae
                       organism = synthetic construct
SEQUENCE: 27
acgttccaag tttggatata catcttcatc cactgtatct tgaact               46

SEQ ID NO: 28          moltype = DNA  length = 42
FEATURE                Location/Qualifiers
source                 1..42
                       mol_type = other DNA
                       note = Reverse inner primer for Erysipelothrix rhusiopathiae
                       organism = synthetic construct
SEQUENCE: 28
gcgaacgcgg ttgttgaatc ctgtagtttc ttccctcttt gt                   42

SEQ ID NO: 29          moltype = DNA  length = 652
FEATURE                Location/Qualifiers
source                 1..652
                       mol_type = other DNA
                       note = DNA sequence of the APX IV gene
                       organism = synthetic construct
SEQUENCE: 29
ccggcaacga cagtaagatt gaaggcacta aaatcacccg taggattgcg ggtaaagaag  60
ttacgcttga tattgccaat cagaaaattg aaaaaggcgt gtcagagaaa ttggggctgt  120
ctgttagtgg ttcggatatc attaaattgt tgtttggagc attgactcca actttaaata  180
gaatgttgct atcacaactc atccagtctt tttccgatag cttggctaaa cttgataatc  240
ccttagcccc ttacactaaa aatggcgtgg tttatgtcac cggcaaaggg aatgatgtgc  300
ttaaaggaac tgaacatgag gatttgtttc tcggtggtga ggggaatgat acttattatg  360
cgagagtagg cgatacaatt gaagacgccg acggcaaagg taaagtctat tttgtgagag  420
aaaaaggggt acctaaggcg gatcctaagc gggtagagtt tagcgagtac ataacgaaag  480
aagaaataaa agaggttgaa aaggggttat taacctacgc agttttagaa aattataatt  540
gggaagagaa aacggcgact ttcgctcatg cgactatgct taatgagctt tttactgatt  600
atactaatta tcgttatgaa gttaaaggac taaaattgcc cgccgttaaa aa         652

SEQ ID NO: 30          moltype = DNA  length = 605
FEATURE                Location/Qualifiers
source                 1..605
                       mol_type = other DNA
                       note = DNA sequence of the OMP P2 gene
                       organism = synthetic construct
SEQUENCE: 30
tcttgcgcca gttcttacga agtcaatttt ctctttaaca ttacctgttt tttcaacacc  60
atgaccacca tcaacagcta cagtaaatgg agcattgaca tatttaagac caaagtatac  120
accatctttg tctttcttat taacagatcc agatttatag tcatcatgag tataacctgc  180
tgccacagtt acagattgac tttccgcaat cttagctgtg tatttagcac ctaaaccaaa  240
gccagattta gcagaaccta cttttacgcc tcccttatca tcacgctcat ttgcaacatt  300
atagttagca cctaacgtca aaccttcaat gcctgtatag gtatagttaa ttgctgaatc  360
agaatctgaa gtaaggatat caaaaccttt tttgtttgtg ttgtttgctg aatatttaat  420
tccaccagta ccaacaccgt atactttatc aaaaccagct tgaccaatgc tatcaccgat  480
tacagcttgt ttaccaaaag aaatttcatg accatagcca cctaaaccga cgtaagcata  540
ttttgtttta acatcgcccc atcctgcagc atttttagaa ttactgtcaa ggcgagtctc  600
ataac                                                            605

SEQ ID NO: 31          moltype = DNA  length = 407
FEATURE                Location/Qualifiers
source                 1..407
                       mol_type = other DNA
                       note = DNA sequence of the invA gene
                       organism = synthetic construct
SEQUENCE: 31
atgcaacatt tggatatcgc tgaattagtt cgttccgcac tggaagtaag tggttgcgat  60
ccttcactca tcggaggaat agatagccat tcaacaattg ttctggattt atttgcattg  120
ccaagtatct gtatcagcgt caaggacgat gatgtatgga tctgggcgca attgggtgct  180
gacagcatgg tggtattaca acagcgggct tatgaaatct taatgaccat aatggaagga  240
```

-continued

```
tgccattttg cccgcggcgg gcaattacta ctgggggagc agaatgggga gctaacgctt  300
aaagccttag tgcatccgga ttttttatct gacggtgaaa agttctctac tgccttgaat  360
gggttttaca actatctgga agtttttagt cggtcgctaa tgagatg                407

SEQ ID NO: 32          moltype = DNA  length = 547
FEATURE                Location/Qualifiers
source                 1..547
                       mol_type = other DNA
                       note = DNA sequence of the DNT gene
                       organism = synthetic construct
SEQUENCE: 32
atcgcgggcg tgctctgcga tctcgagagc gcgcagcgca cgttgcccgt cgtattggcc  60
aggtttcggc cccttggcgt gcttgcgcga ttcagaaggc tggagcagga aaccgcgggc  120
atgctgcttg gcgaccagga gccggagcct cggggcttca tcagttttac cgattttcgc  180
gatagcgacg cgttcgccag ctacgcggag tatgcggccc agttcaacga ctatatcgat  240
caatacagca tactcgaggc gcagcggctg gcgcggattc tggccctggg ctcgcggatg  300
acggtcgatc aatggtgcct tcccctgcag aaagtacggc actacaaggt gctgacatcg  360
cagccagggc tgatcgcgcg tggaatcgaa aatcacaaca ggggcattga atattgcctg  420
gggcggccgc cgctgaccga tctgccgggt cttttcacca tgttccagct ccatgattcc  480
agctggctgt tggtatcgaa catcaacggt gagctttggt ctgatgtcct tgcgaacgct  540
gaggtga                                                             547

SEQ ID NO: 33          moltype = DNA  length = 457
FEATURE                Location/Qualifiers
source                 1..457
                       mol_type = other DNA
                       note = DNA sequence of the kmt1 gene
                       organism = synthetic construct
SEQUENCE: 33
gctgtaaacg aactcgccac tttttgtttc atttggactg acacgatcaa accgttgaac  60
acgaagaaaa agaccaaaat aggtaaccaa tacacgataa ataaattaaa ccgctctgcc  120
gttaatggct tcaataatgg ccataagaaa cgtaactcaa catggaaata ttgataaatc  180
agactgacaa ggaaatataa accggcaaat aacaataagc tgagtaataa ataacgtcca  240
atcagttgcg ccgttgtcaa ggaagcagat tggctcaaca caccaaactc cgcccaacaa  300
aactgtgctt ttctttgcca cacgccaaat aaaagactac cgacaagccc actcacaacg  360
agccataaaa taatgccatt tcccatttca agtggcataa aactcaattt cgcggcaatc  420
ggttcattcg caccgcccca ctgggtaaat agcggat                            457

SEQ ID NO: 34          moltype = DNA  length = 689
FEATURE                Location/Qualifiers
source                 1..689
                       mol_type = other DNA
                       note = DNA sequence of the gdh gene
                       organism = synthetic construct
SEQUENCE: 34
gcagcgtatt ctgtcaaacg agcgcggcgt ttttctttga tgtccaccaa gaggtcgaag  60
tcgataccag tttcgtcaat gatgtaacca tttgagtctg aaacagaaat aacttttgca  120
ccaagttcag tcgctttttg aacagcatat tgggcaacgt taccagaacc tgagataagg  180
acagtttggt ctttgaagga tttaccgttt gctgccaaca tgttatcagt gaagtaaacc  240
aaaccgtaac cagttgcttc tgggcggatc aatgaaccac cgaagccaag aggtttacca  300
gtcaagacac ctgcatcaaa ctggcggagg cgtttgtatt gaccgtacat gtaaccgatc  360
tcacgaccac cgacaccgat gtcaccagca gggacgtcaa gtgaaggtcc gatgtgtttt  420
tgcaattcag tcatgaagct ttggcagaag cgcatgattt cagcatcagt tttccttta   480
ggatcaaagt ctgaaccacc tttaccaccg ccgattggaa gaccagtcaa gacgtttttg  540
aagatttgct caaaaccgag gaacttcaag atggattggt ttacagttgg gtggaagcga  600
agaccgcctt tataaggacc tacagctgag ttgaactgaa cacggtagcc acggttgact  660
tgaacatttc catctttatc tgtccatgg                                     689

SEQ ID NO: 35          moltype = DNA  length = 1881
FEATURE                Location/Qualifiers
source                 1..1881
                       mol_type = other DNA
                       note = DNA sequence of the spaA gene
                       organism = synthetic construct
SEQUENCE: 35
atgaaaaaga aaaaacacct atttccgaaa gtaagtctta tgtcgtgctt acttttaaca  60
gcaatgccac tacaaacagc ttttgctgat tcgacagata tttctgtgat tccactaatc  120
ggtgaacaag ttggattgct cccagtttta cctgggacag gggtacatgc tcaggaatac  180
aacaaaatga ctgatgctta tattgaaaaa ttggtatctc taattaatca aaaagtgaag  240
ccgtttctta taaatgaacc aaaggggtac caaagtttcg aagcagtgaa tgaagagatt  300
aactcgattg taagtgaact taaaaatgaa ggaatgagtc ttcaaaacat tcaccatatg  360
tttaaacaaa gcatccaaaa cctagcaact agaatcggct acagaagttt tatgcaggat  420
gctatgtatc ttgaaaattt tgaaagatta acgattcctg aacttgatga agcatacgtt  480
gatttactcg tgaattacga ggtgaaacac cgtattttag taaaatatga aggtaaagtt  540
aaaggtagag ctcccttaga agcatttata gttcctctaa gagatagaat tcgtagtatg  600
aatgaaattg ctgcagaagt aaattattta cctgaagcgc atgaggattt cttagtttca  660
gattcaagcg agtataatga caaactaaat aatatcaact ttgctttggg tctaggggtc  720
agcgagttta ttgactataa ccggctcgaa aatatgatgg aaaaagaact tcatccactg  780
tatcttgaac tttatgctat gcggagaaat cgccaaattc aagttgtaag agatgtatat  840
```

-continued

```
ccaaacttgg aacgtgcgaa cgcggttgtt gaatccttaa agacaattaa agatataaaa  900
caaagaggga agaaactaca ggaacttctt gaaatttata tccaaagaag tggagatgtt  960
cgaaaaccag atgtactcca acgatttatt ggaaaatatc aatcagtagt tgatgaagaa  1020
aaaaataaac ttcaagatta tttagaatca gatatttttg attcatatag tgtggatggc  1080
gagaaaataa gaaataaaga aattacactc atcaatagag atgcatactt atctatgatt  1140
tacagagctc aatcgatttc ggaaattaag acgattcgtg cagatttaga atcacttgtc  1200
aaatcattcc aaaatgaaga aagtgactct aaagtagagc ctgaaagtcc cgttaaagta  1260
gaaaaaccag ttgatgaaga aaaacctaaa gatcaaaaga agctagttga tcaatcaaaa  1320
cccgaatcga attcaaaaga agggtggatt aagaaagata ataagtggtt ctatattgag  1380
aaatcaggtg gaatggcaac aggttggaag aaggtagcag acaaatggta ctacctcgat  1440
aatacgggtg ctatagttac gggttggaag aaggtagcaa acaaatggta ctatcttgaa  1500
aaatcaggtg cgatggcaac aggatggaag aaagtatcaa acaagtggta ctaccttgaa  1560
aactcaggtg caatggcaac aggatggaag aaagtatcaa acaagtggta ctaccttgaa  1620
aattcaggcg caatggctac aggatggaaa aaggtagcaa acaaatggta ctaccttgaa  1680
aactcaggtg cgatggcaac aggatggaag aaagtatcga acaagtggta ctaccttgaa  1740
aactcaggcg caatggctac aggatggaaa aaggtagcaa acaaatggta ctaccttgat  1800
aaatcaggaa tgatggttac aggttcaaaa tctattgatg gtaaaaagta tgcatttaag  1860
aacgatggaa gtttaaaata g                                            1881
```

LOOP-MEDIATED ISOTHERMAL AMPLIFICATION (LAMP) PRIMER SETS FOR DETECTING PORCINE SUSCEPTIBILITY-RELATED PATHOGENIC BACTERIA, AND KIT, LAMP CHIP AND USE BASED ON THE SAME

TECHNICAL FIELD

The present disclosure belongs to the technical field of preparation of LAMP detection reagents, in particular to loop-mediated isothermal amplification (LAMP) primer sets for detecting porcine susceptibility-related pathogenic bacteria, and a kit, a LAMP chip and use based on the same.

BACKGROUND ART

The continuous improvement of large-scale breeding can effectively improve the efficiency of breeding industry. However, this breeding mode may increase a probability of diseases in swine herds, and may also bring new challenges to the control of infectious diseases. At present, diseases are the first major factor restricting the development of pig industry; as far as the current situation of swine diseases is concerned, the mixed infection of various pathogenic bacteria is a trend of disease development in swine farms. Among them, swine respiratory and reproductive diseases caused by pathogenic bacteria such as *Bordetella bronchiseptica, Salmonella choleraesuis*, and *Pasteurella multocida* each have a gradually increasing incidence rate.

Swine-derived diseases show a diversified development trend, further increasing the difficulty of disease control. To control the swine-derived diseases, it is the key for swine disease control to establish a rapid detection mechanism for mixed pathogenic bacteria in swine farms.

Detection techniques for porcine susceptibility-related pathogenic bacteria mainly include traditional microbiological diagnosis, serological diagnosis, and molecular biology-based diagnosis. Currently, the molecular biology-based diagnosis represented by PCR and derivative detection techniques thereof occupy a dominant position. However, the above techniques each have certain limitations, such as a cumbersome testing process, heavy workload, and high requirements for testing instruments. Therefore, it is urgent to develop a rapid and simple detection method capable of detecting multiple pathogenic bacteria simultaneously in scientific research and production practice.

SUMMARY

To solve the above problems, the present disclosure provides LAMP primer sets for detecting porcine susceptibility-related pathogenic bacteria, and a kit, a LAMP chip and use based on the same. The multiple LAMP primer sets have a high sensitivity and strong specificity, and can simultaneously detect multiple types of pathogenic bacteria.

To achieve the above objective, the present disclosure provides the following technical solutions.

The present disclosure provides LAMP primer sets for detecting porcine susceptibility-related pathogenic bacteria, where the porcine susceptibility-related pathogenic bacteria include: *Actinobacillus pleuropneumoniae* (*A. pleuropneumoniae*), *Haemophilus parasuis* (*H. parasuis*), *Salmonella choleraesuis* (*S. choleraesuis*), *Bordetella bronchiseptica* (*B. bronchiseptica*), *Pasteurella multocida* (*P. multocida*), *Streptococcus suis* (*S. suis*), and *Erysipelothrix rhusiopathiae* (*E. rhusiopathiae*); and the LAMP primer sets include an *A. pleuropneumoniae* primer set, an *H. parasuis* primer set, an *S. choleraesuis* primer set, a *B. bronchiseptica* primer set, a *P. multocida* primer set, an *S. suis* primer set, and an *E. rhusiopathiae* primer set;

The *A. pleuropneumoniae* primer set includes a forward outer primer F3 with the nucleotide sequence set forth in SEQ ID NO: 1, a reverse outer primer B3 with the nucleotide sequence set forth in SEQ ID NO: 2, a forward inner primer FIP with the nucleotide sequence set forth in SEQ ID NO: 3, and a reverse inner primer BIP with the nucleotide sequence set forth in SEQ ID NO: 4;

The *H. parasuis* primer set includes a forward outer primer F3 with the nucleotide sequence set forth in SEQ ID NO: 5, a reverse outer primer B3 with the nucleotide sequence set forth in SEQ ID NO: 6, a forward inner primer FIP with the nucleotide sequence set forth in SEQ ID NO: 7, and a reverse inner primer BIP with the nucleotide sequence set forth in SEQ ID NO: 8;

The *S. choleraesuis* primer set includes a forward outer primer F3 with the nucleotide sequence set forth in SEQ ID NO: 9, a reverse outer primer B3 with the nucleotide sequence set forth in SEQ ID NO: 10, a forward inner primer FIP with the nucleotide sequence set forth in SEQ ID NO: 11, and a reverse inner primer BIP with the nucleotide sequence set forth in SEQ ID NO: 12;

The *B. bronchiseptica* primer set includes a forward outer primer F3 with the nucleotide sequence set forth in SEQ ID NO: 13, a reverse outer primer B3 with the nucleotide sequence set forth in SEQ ID NO: 14, a forward inner primer FIP with the nucleotide sequence set forth in SEQ ID NO: 15, and a reverse inner primer BIP with the nucleotide sequence set forth in SEQ ID NO: 16;

The *P. multocida* primer set includes a forward outer primer F3 with the nucleotide sequence set forth in SEQ ID NO: 17, a reverse outer primer B3 with the nucleotide sequence set forth in SEQ ID NO: 18, a forward inner primer FIP with the nucleotide sequence set forth in SEQ ID NO: 19, and a reverse inner primer BIP with the nucleotide sequence set forth in SEQ ID NO: 20;

The *S. suis* primer set includes a forward outer primer F3 with the nucleotide sequence set forth in SEQ ID NO: 21, a reverse outer primer B3 with the nucleotide sequence set forth in SEQ ID NO: 22, a forward inner primer FIP with the nucleotide sequence set forth in SEQ ID NO: 23, and a reverse inner primer BIP with the nucleotide sequence set forth in SEQ ID NO: 24; and The *E. rhusiopathiae* primer set includes a forward outer primer F3 with the nucleotide sequence set forth in SEQ ID NO: 25, a reverse outer primer B3 with the nucleotide sequence set forth in SEQ ID NO: 26, a forward inner primer FIP with the nucleotide sequence set forth in SEQ ID NO: 27, and a reverse inner primer BIP with the nucleotide sequence set forth in SEQ ID NO: 28.

The present disclosure further provides a kit of porcine susceptibility-related pathogenic bacteria, including the LAMP primer sets and a reaction buffer.

In some embodiments, the reaction buffer may include Bst DNA Polymerase, a 10× Isothermal Amplification Reaction Buffer, BSA-A, dNTP, an $MgSO_4$ aqueous solution, and a fluorescent dye.

The present disclosure further provides a LAMP chip for detecting porcine susceptibility-related pathogenic bacteria, including the LAMP primer sets, a reaction buffer, and a chip.

In some embodiments, in the LAMP primer sets, an outer primer pair and an inner primer pair corresponding to any one of the pathogenic bacteria may have a molar ratio of 1:8.

In some embodiments, the reaction buffer may include Bst DNA Polymerase, a 10× Isothermal Amplification Reaction Buffer, BSA-A, dNTP, an $MgSO_4$ aqueous solution, and a fluorescent dye.

In some embodiments, the chip may include an isothermal amplification microfluidic chip.

In some embodiments, an amplification reaction cell of the LAMP chip may include: an *H. parasuis* reaction cell, an *S. choleraesuis* reaction cell, a *B. bronchiseptica* reaction cell, a *P. multocida* reaction cell, an *S. suis* reaction cell, an *E. rhusiopathiae* reaction cell, an *A. pleuropneumoniae* reaction cell, and a negative control reaction cell.

The present disclosure provides LAMP primer sets for detecting porcine susceptibility-related pathogenic bacteria, including an *A. pleuropneumoniae* primer set, an *H. parasuis* primer set, an *S. choleraesuis* primer set, a *B. bronchiseptica* primer set, a *P. multocida* primer set, an *S. suis* primer set, and an *E. rhusiopathiae* primer set. In the present disclosure, an *A. pleuropneumoniae* APX IV gene, an *H. parasuis* OMP P2 gene, an *S. choleraesuis* invA gene, a *B. bronchiseptica* DNT gene, a *P. multocida* kmt1 gene, an *S. suis* gdh gene, and an *E. rhusiopathiae* spaA gene are used as target genes for detection, and LAMP primer sets with a high specificity and desirable sensitivity are designed for the microfluidic chip technology. The LAMP primer sets each have a high specificity and desirable sensitivity, have no cross reaction when detecting, and may accurately determine a disease type. The LAMP primer sets are capable of being applied to the detection using a microfluidic chip technology, to rapidly, efficiently and highly-specifically amplify a target gene sequence under isothermal conditions within 1 h; moreover, the LAMP primer sets have simplicity and efficiency, which are more suitable for grassroots applicability.

DETAILED DESCRIPTION OF THE EMBODIMENTS

Figure 1:
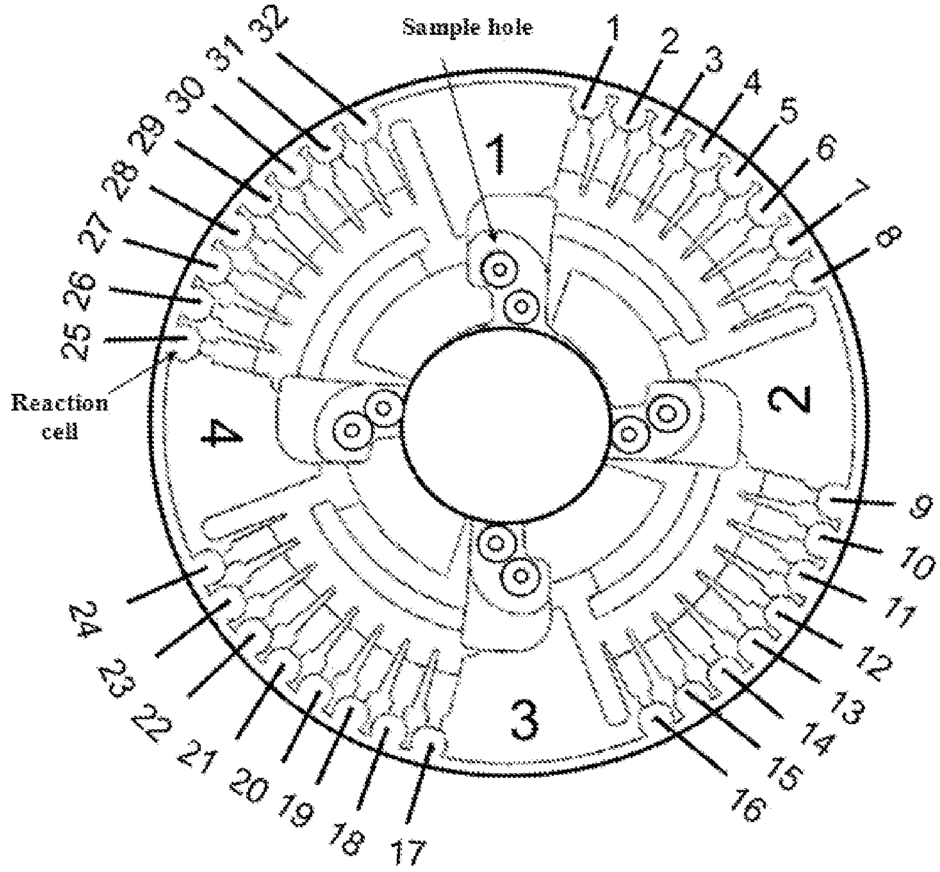
FIG. 1 shows a schematic diagram of a disc-type microfluidic chip and a primer spotting cell provided in examples.

The present disclosure provides LAMP primer sets for detecting porcine susceptibility-related pathogenic bacteria, where the porcine susceptibility-related pathogenic bacteria include: *A. pleuropneumoniae, H. parasuis, S. choleraesuis, B. bronchiseptica, P. multocida, S. suis*, and *E. rhusiopathiae*; and the LAMP primer sets include an *A. pleuropneumoniae* primer set, an *H. parasuis* primer set, an *S. choleraesuis* primer set, a *B. bronchiseptica* primer set, a *P. multocida* primer set, an *S. suis* primer set, and an *E. rhusiopathiae* primer set;

The *A. pleuropneumoniae* primer set includes a forward outer primer F3 with the nucleotide sequence set forth in SEQ ID NO: 1, a reverse outer primer B3 with the nucleotide sequence set forth in SEQ ID NO: 2, a forward inner primer FIP with the nucleotide sequence set forth in SEQ ID NO: 3, and a reverse inner primer BIP with the nucleotide sequence set forth in SEQ ID NO: 4;

The *H. parasuis* primer set includes a forward outer primer F3 with the nucleotide sequence set forth in SEQ ID NO: 5, a reverse outer primer B3 with the nucleotide sequence set forth in SEQ ID NO: 6, a forward inner primer FIP with the nucleotide sequence set forth in SEQ ID NO: 7, and a reverse inner primer BIP with the nucleotide sequence set forth in SEQ ID NO: 8;

The *S. choleraesuis* primer set includes a forward outer primer F3 with the nucleotide sequence set forth in SEQ ID NO: 9, a reverse outer primer B3 with the nucleotide sequence set forth in SEQ ID NO: 10, a forward inner primer FIP with the nucleotide sequence set forth in SEQ ID NO: 11, and a reverse inner primer BIP with the nucleotide sequence set forth in SEQ The *B. bronchiseptica* primer set includes a forward outer primer F3 with the nucleotide sequence set forth in SEQ ID NO: 13, a reverse outer primer B3 with the nucleotide sequence set forth in SEQ ID NO: 14, a forward inner primer FIP with the nucleotide sequence set forth in SEQ ID NO: 15, and a reverse inner primer BIP with the nucleotide sequence set forth in SEQ ID NO: 16;

The *P. multocida* primer set includes a forward outer primer F3 with the nucleotide sequence set forth in SEQ ID NO: 17, a reverse outer primer B3 with the nucleotide sequence set forth in SEQ ID NO: 18, a forward inner primer FIP with the nucleotide sequence set forth in SEQ ID NO: 19, and a reverse inner primer BIP with the nucleotide sequence set forth in SEQ ID NO: 20;

The *S. suis* primer set includes a forward outer primer F3 with the nucleotide sequence set forth in SEQ ID NO: 21, a reverse outer primer B3 with the nucleotide sequence set forth in SEQ ID NO: 22, a forward inner primer FIP with the nucleotide sequence set forth in SEQ ID NO: 23, and a reverse inner primer BIP with the nucleotide sequence set forth in SEQ ID NO: 24; and The *E. rhusiopathiae* primer set includes a forward outer primer F3 with the nucleotide sequence set forth in SEQ ID NO: 25, a reverse outer primer B3 with the nucleotide sequence set forth in SEQ ID NO: 26, a forward inner primer FIP with the nucleotide sequence set forth in SEQ ID NO: 27, and a reverse inner primer BIP with the nucleotide sequence set forth in SEQ ID NO: 28. The LAMP primer sets have a high specificity and desirable sensitivity.

The present disclosure further provides a kit of porcine susceptibility-related pathogenic bacteria, including the LAMP primer sets and a reaction buffer. In some embodiments, the reaction buffer includes a 10× Isothermal Amplification Reaction Buffer, BSA-A, dNTP, an $MgSO_4$ aqueous solution, a fluorescent dye, and Bst DNA Polymerase; and the fluorescent dye is preferably SYTO™9.

The present disclosure further provides a LAMP chip for detecting porcine susceptibility-related pathogenic bacteria, including the LAMP primer sets, a reaction buffer, and a chip. In some embodiments, the chip includes an isothermal amplification microfluidic chip, preferably a 32-well reaction cell disc-type microfluidic chip, and more preferably a microfluidic chip shown in FIG. 1. In some embodiments, the microfluidic chip used in the experiment of the present disclosure is a 4×8 microfluidic chip produced by Shanghai Igenetec Diagnostics Co., Ltd.; the microfluidic chip preferably includes 4 test zones; each of the test zone preferably includes a sample hole and a reaction cell; the test zones preferably include 8 reaction cells; and the reaction cells preferably include: an *H. parasuis* reaction cell, an *S. choleraesuis* reaction cell, a *B. bronchiseptica* reaction cell, a *P. multocida* reaction cell, an *S. suis* reaction cell, an *E. rhusiopathiae* reaction cell, an *A. pleuropneumoniae* reaction cell, and a negative control reaction cell. The present disclosure provides a real-time detection technology combining the microfluidic chip with a LAMP technology, which may establish an efficient, rapid, sensitive and specific real-time detection technology, and provides more significance in the detection of porcine susceptibility-related pathogenic bacteria and a basis for boosting the rapid detection of pathogenic bacteria.

In some embodiments of the present disclosure, in the LAMP primer sets, an outer primer pair and an inner primer pair corresponding to any one of the pathogenic bacteria have a molar ratio of preferably 1:8; the reaction buffer preferably includes an isothermal amplification buffer and an isothermal amplification enzyme solution; the isothermal amplification buffer preferably includes a 10× Isothermal Amplification Reaction Buffer, BSA-A, dNTP, a $MgSO_4$ aqueous solution, and a fluorescent dye, and the isothermal amplification enzyme solution preferably includes Bst DNA Polymerase; and the fluorescent dye is more preferably SYTO™9. The LAMP chip may effectively improve the detection efficiency of the LAMP chip by selecting a specific reaction buffer.

In some embodiments of the present disclosure, after the LAMP primer sets of different pathogenic bacteria is obtained, the LAMP primer sets of the corresponding pathogenic bacteria are coated into the reaction cells corresponding to the microfluidic chip, to obtain a microfluidic chip coated with the LAMP primer sets. The outer primer pair and the inner primer pair corresponding to the pathogenic bacteria are preferably mixed in a molar ratio of 1:8, and then added to the reaction cells of the microfluidic chip; in some embodiments, a LAMP primer set corresponding to a pathogenic bacterium is added in each reaction cell; after the LAMP primer sets of all pathogenic bacteria are added to the reaction cells, vacuum heating and drying, compressing, film sealing and molding treatment are preferably conducted, such that the LAMP primer set is coated into the reaction cells.

After the microfluidic chip coated with the LAMP primer set is obtained, an unknown sample is preferably coated onto an injection zone of the microfluidic chip for amplification. The unknown sample, the isothermal amplification buffer (the 10× Isothermal Amplification Reaction Buffer, the BSA-A, the dNTP, the $MgSO_4$ aqueous solution, and the fluorescent dye), and the isothermal amplification enzyme solution (Bst DNA Polymerase) are preferably mixed to obtain a reaction mixture before the coating of the unknown sample; the reaction mixture is coated to the injection zone of the microfluidic chip coated with the LAMP primer set, followed by sealing with a sealing film, and the microfluidic chip is placed in a detection device for real-time amplification detection.

After the amplification is completed, in some embodiments of the present disclosure, a fluorescence intensity-time curve is plotted based on an amplification trend in each reaction cell through changes of fluorescence values, to determine whether a sample in each amplification reaction well is negative or positive. Namely, if the unknown sample shows an S-shaped curve, and a blank control shows no amplification curve, it is determined that the unknown sample is positive for the corresponding pathogenic bacteria.

In order to further illustrate the present disclosure, the LAMP primer sets for detecting porcine susceptibility-related pathogenic bacteria, and the kit, the LAMP chip and the use based on the same provided by the present disclosure are described in detail below with reference to the accompanying drawings and examples, but the accompanying drawings and the examples should not be construed as limiting the protection scope of the present disclosure.

Example 1

Design and preparation of LAMP primer sets for detecting porcine susceptibility-related pathogenic bacteria 1. Sequence Acquisition:

(1) Obtaining an *A. pleuropneumoniae* APX IV gene sequence: a nucleic acid sequence of the APX IV gene was downloaded from the GenBank public database

```
(as set forth in SEQ ID NO: 29:
CCGGCAACGACAGTAAGATTGAAGGCACTAAAATCA
CCCGTAGGATTGCGGGTAAAGAAGTTACGCTTGATA
TTGCCAATCAGAAAATTGAAAAAGGCGTGTCAGAGA
AATTGGGGCTGTCTGTTAGTGGTTCGGATATCATTA
AATTGTTGTTTGGAGCATTGACTCCAACTTTAAATA
GAATGTTGCTATCACAACTCATCCAGTCTTTTTCCG
ATAGCTTGGCTAAACTTGATAATCCCTTAGCCCCTT
ACACTAAAAATGGCGTGGTTTATGTCACCGGCAAAG
GGAATGATGTGCTTAAAGGAACTGAACATGAGGATT
TGTTTCTCGGTGGTGAGGGGAATGATACTTATTATG
CGAGAGTAGGCGATACAATTGAAGACGCCGACGGCA
AAGGTAAAGTCTATTTTGTGAGAGAAAAAGGGGTAC
CTAAGGCGGATCCTAAGCGGGTAGAGTTTAGCGAGT
ACATAACGAAAGAAGAAATAAAAGAGGTTGAAAAGG
GGTTATTAACCTACGCAGTTTTAGAAAATTATAATT
GGGAAGAGAAAACGGCGACTTTCGCTCATGCGACTA
TGCTTAATGAGCTTTTTACTGATTATACTAATTATC
GTTATGAAGTTAAAGGACTAAAATTGCCCGCCGTTA
AAAA);
```

(2) Obtaining an *H. parasuis* OMP P2 gene sequence: a nucleic acid sequence of the OMP P2 gene (as set forth in SEQ ID NO: 30:
TCTTGCGCCAGTTCTTACGAAGTCAATTTTCTCTTT
AACATTACCTGTTTTTTCAACACCATGACCACCATC
AACAGCTACAGTAAATGGAGCATTGACATATTTAAG
ACCAAAGTATACACCATCTTTGTCTTTCTTATTAAC
AGATCCAGATTTATAGTCATCATGAGTATAACCTGC
TGCCACAGTTACAGATTGACTTTCCGCAATCTTAGC
TGTGTATTTAGCACCTAAACCAAAGCCAGATTTAGC
AGAACCTACTTTTACGCCTCCCTTATCATCACGCTC
ATTTGCAACATTATAGTTAGCACCTAACGTCAAACC
TTCAATGCCTGTATAGGTATAGTTAATTGCTGAATC
AGAATCTGAAGTAAGGATATCAAAACCTTTTTTGTT
TGTGTTGTTTGCTGAATATTTAATTCCACCAGTACC
AACACCGTATACTTTATCAAAACCAGCTTGACCAAT
GCTATCACCGATTACAGCTTGTTTACCAAAAGAAAT
TTCATGACCATAGCCACCTAAACCGACGTAAGCATA
TTTTGTTTTAACATCGCCCCATCCTGCAGCATTTTT
AGAATTACTGTCAAGGCGAGTCTCATAAC);

(3) Obtaining an *S. choleraesuis* invA gene sequence: a nucleic acid sequence of the invA gene (as set forth in SEQ ID NO: 31:
ATGCAACATTTGGATATCGCTGAATTAGTTCGTTCC
GCACTGGAAGTAAGTGGTTGCGATCCTTCACTCATC
GGAGGAATAGATAGCCATTCAACAATTGTTCTGGAT
TTATTTGCATTGCCAAGTATCTGTATCAGCGTCAAG
GACGATGATGTATGGATCTGGGCGCAATTGGGTGCT
GACAGCATGGTGGTATTACAACAGCGGGCTTATGAA
ATCTTAATGACCATAATGGAAGGATGCCATTTTGCC
CGCGGCGGGCAATTACTACTGGGGGAGCAGAATGGG
GAGCTAACGCTTAAAGCCTTAGTGCATCCGGATTTT
TTATCTGACGGTGAAAAGTTCTCTACTGCCTTGAAT
GGGTTTTACAACTATCTGGAAGTTTTTAGTCGGTCG
CTAATGAGATG);

(4) Obtaining a *B. bronchiseptica* DNT gene sequence: a nucleic acid sequence of the DNT gene (as set forth in SEQ ID NO: 32:
ATCGCGGGCGTGCTCTGCGATCTCGAGAGCGCGCAG
CGCACGTTGCCCGTCGTATTGGCCAGGTTTCGGCCC
CTTGGCGTGCTTGCGCGATTCAGAAGGCTGGAGCAG
GAAACCGCGGGCATGCTGCTTGGCGACCAGGAGCCG -continued GAGCCTCGGGGCTTCATCAGTTTTACCGATTTTCGC
GATAGCGACGCGTTCGCCAGCTACGCGGAGTATGCG
GCCCAGTTCAACGACTATATCGATCAATACAGCATA
CTCGAGGCGCAGCGGCTGGCGCGGATTCTGGCCCTG
GGCTCGCGGATGACGGTCGATCAATGGTGCCTTCCC
CTGCAGAAAGTACGGCACTACAAGGTGCTGACATCG
CAGCCAGGGCTGATCGCGCGTGGAATCGAAAATCAC
AACAGGGGCATTGAATATTGCCTGGGGCGGCCGCCG
CTGACCGATCTGCCGGGTCTTTTCACCATGTTCCAG
CTCCATGATTCCAGCTGGCTGTTGGTATCGAACATC
AACGGTGAGCTTTGGTCTGATGTCCTTGCGAACGCT
GAGGTGA);

(5) Obtaining a *P. multocida* kmt1 gene sequence: a nucleic acid sequence of the kmt1 gene (as set forth in SEQ ID NO: 33:
GCTGTAAACGAACTCGCCACTTTTTGTTTCATTTGG
ACTGACACGATCAAACCGTTGAACACGAAGAAAAAG
ACCAAAATAGGTAACCAATACACGATAAATAAATTA
AACCGCTCTGCCGTTAATGGCTTCAATAATGGCCAT
AAGAAACGTAACTCAACATGGAAATATTGATAAATC
AGACTGACAAGGAAATATAAACCGGCAAATAACAAT
AAGCTGAGTAATAAATAACGTCCAATCAGTTGCGCC
GTTGTCAAGGAAGCAGATTGGCTCAACACACCAAAC
TCCGCCCAACAAAACTGTGCTTTTCTTTGCCACACG
CCAAATAAAAGACTACCGACAAGCCCACTCACAACG
AGCCATAAAATAATGCCATTTCCCATTTCAAGTGGC
ATAAAACTCAATTTCGCGGCAATCGGTTCATTCGCA
CCGCCCCACTGGGTAAATAGCGGAT);

(6) Obtaining an *S. suis* gdh gene sequence: a nucleic acid sequence of the gdh gene (as set forth in SEQ ID NO: 34:
GCAGCGTATTCTGTCAAACGAGCGCGGCGTTTTTCT
TTGATGTCCACCAAGAGGTCGAAGTCGATACCAGTT
TCGTCAATGATGTAACCATTTGAGTCTGAAACAGAA
ATAACTTTTGCACCAAGTTCAGTCGCTTTTTGAACA
GCATATTGGGCAACGTTACCAGAACCTGAGATAAGG
ACAGTTTGGTCTTTGAAGGATTTACCGTTTGCTGCC
AACATGTTATCAGTGAAGTAAACCAAACCGTAACCA
GTTGCTTCTGGGCGGATCAATGAACCACCGAAGCCA
AGAGGTTTACCAGTCAAGACACCTGCATCAAACTGG -continued

CGGAGGCGTTTGTATTGACCGTACATGTAACCGATC

TCACGACCACCGACACCGATGTCACCAGCAGGGACG

TCAAGTGAAGGTCCGATGTGTTTTTGCAATTCAGTC

ATGAAGCTTTGGCAGAAGCGCATGATTTCAGCATCA

GTTTTTCCTTTAGGATCAAAGTCTGAACCACCTTTA

CCACCGCCGATTGGAAGACCAGTCAAGACGTTTTTG

AAGATTTGCTCAAAACCGAGGAACTTCAAGATGGAT

TGGTTTACAGTTGGGTGGAAGCGAAGACCGCCTTTA

TAAGGACCTACAGCTGAGTTGAACTGAACACGGTAG

CCACGGTTGACTTGAACATTTCCATCTTTATCTGTC

CATGG);

and (7) Obtaining an *E. rhusiopathiae* spaA gene sequence: a nucleic acid sequence of the spaA gene (as set forth in SEQ ID NO: 35:
ATGAAAAAGAAAAAACACCTATTTCCGAAAGTAAGT

CTTATGTCGTGCTTACTTTTAACAGCAATGCCACTA

CAAACAGCTTTTGCTGATTCGACAGATATTTCTGTG

ATTCCACTAATCGGTGAACAAGTTGGATTGCTCCCA

GTTTTACCTGGGACAGGGGTACATGCTCAGGAATAC

AACAAAATGACTGATGCTTATATTGAAAAATTGGTA

TCTCTAATTAATCAAAAAGTGAAGCCGTTTCTTATA

AATGAACCAAAGGGGTACCAAAGTTTCGAAGCAGTG

AATGAAGAGATTAACTCGATTGTAAGTGAACTTAAA

AATGAAGGAATGAGTCTTCAAAACATTCACCATATG

TTTAAACAAAGCATCCAAAACCTAGCAACTAGAATC

GGCTACAGAAGTTTTATGCAGGATGCTATGTATCTT

GAAAATTTTGAAAGATTAACGATTCCTGAACTTGAT

GAAGCATACGTTGATTTACTCGTGAATTACGAGGTG

AAACACCGTATTTTAGTAAAATATGAAGGTAAAGTT

AAAGGTAGAGCTCCCTTAGAAGCATTTATAGTTCCT

CTAAGAGATAGAATTCGTAGTATGAATGAAATTGCT

GCAGAAGTAAATTATTTACCTGAAGCGCATGAGGAT

TTCTTAGTTTCAGATTCAAGCGAGTATAATGACAAA

CTAAATAATATCAACTTTGCTTTGGGTCTAGGGGTC

AGCGAGTTTATTGACTATAACCGGCTCGAAAATATG

ATGGAAAAAGAACTTCATCCACTGTATCTTGAACTT

TATGCTATGCGGAGAAATCGCCAAATTCAAGTTGTA

AGAGATGTATATCCAAACTTGGAACGTGCGAACGCG

GTTGTTGAATCCTTAAAGACAATTAAAGATATAAAA

CAAAGAGGGAAGAAACTACAGGAACTTCTTGAAATT

-continued

TATATCCAAAGAAGTGGAGATGTTCGAAAACCAGAT

GTACTCCAACGATTTATTGGAAAATATCAATCAGTA

GTTGATGAAGAAAAAAATAAACTTCAAGATTATTTA

GAATCAGATATTTTTGATTCATATAGTGTGGATGGC

GAGAAAATAAGAAATAAAGAAATTACACTCATCAAT

AGAGATGCATACTTATCTATGATTTACAGAGCTCAA

TCGATTTCGGAAATTAAGACGATTCGTGCAGATTTA

GAATCACTTGTCAAATCATTCCAAAATGAAGAAAGT

GACTCTAAAGTAGAGCCTGAAAGTCCCGTTAAAGTA

GAAAAACCAGTTGATGAAGAAAAACCTAAAGATCAA

AAGAAGCTAGTTGATCAATCAAAACCCGAATCGAAT

TCAAAAGAAGGGTGGATTAAGAAAGATAATAAGTGG

TTCTATATTGAGAAATCAGGTGGAATGGCAACAGGT

TGGAAGAAGGTAGCAGACAAATGGTACTACCTCGAT

AATACGGGTGCTATAGTTACGGGTTGGAAGAAGGTA

GCAAACAAATGGTACTATCTTGAAAAATCAGGTGCG

ATGGCAACAGGATGGAAGAAAGTATCAAACAAGTGG

TACTACCTTGAAAACTCAGGTGCAATGGCAACAGGA

TGGAAGAAAGTATCAAACAAGTGGTACTACCTTGAA

AATTCAGGCGCAATGGCTACAGGATGGAAAAAGGTA

GCAAACAAATGGTACTACCTTGAAAACTCAGGTGCG

ATGGCAACAGGATGGAAGAAAGTATCGAACAAGTGG

TACTACCTTGAAAACTCAGGCGCAATGGCTACAGGA

TGGAAAAAGGTAGCAAACAAATGGTACTACCTTGAT

AAATCAGGAATGATGGTTACAGGTTCAAAATCTATT

GATGGTAAAAAGTATGCATTTAAGAACGATGGAAGT

TTAAAATAG).

2. Primer Design (1) Specific gene primers: conserved segments of the above-mentioned specific genes were determined, and LAMP primer sets were designed for the conserved segments.

(2) Synthesis of primers: the primer sequences in Table 1 were entrusted to synthesize by Tsingke Biotechnology Co., Ltd.

In this example, the 28 primers designed were shown in Table 1.

TABLE 1

Primer sequences in primer sets

| Primer ID | Primer sequence (5'-3') | Pathogenic bacteria |
|---|---|---|
| SEQ ID NO. 1 | F3: CCCTTAGCCCCTTACACTA | *A. pleuropneumoniae* (APP) |

TABLE 1-continued

Primer sequences in primer sets

| Primer ID | Primer sequence (5'-3') | Pathogenic bacteria |
|---|---|---|
| SEQ ID NO. 2 | B3: CGCTTAGGATCCGCCTTA | |
| SEQ ID NO. 3 | FIP: CACCACCGAGAAACAAATCCTCGGCGTGGTTTATGTCACC | |
| SEQ ID NO. 4 | BIP: AGGCGATACAATTGAAGACGCCGGTACCCCTTTTTCTCTCACCAC | |
| SEQ ID NO. 5 | F3: ACCTACTTTTACGCCTCC | *H. parasuis* (HPS) |
| SEQ ID NO. 6 | B3: GCATTGGTCAAGCTGGTT | |
| SEQ ID NO. 7 | FIP: CAGGCATTGAAGGTTTGACGTTTATCATCACGCTCATTTGC | |
| SEQ ID NO. 8 | BIP: ACCTTTTTTGTTTGTGTTGTTTGCTAAAGTATAGGTGTTGGTACTG | |
| SEQ ID NO. 9 | F3: CATTGCCAAGTATCTGTATCAGC | *S. choleraesuis* (Sal) |
| SEQ ID NO. 10 | B3: CCGGATGCACTAAGGCTTTA | |
| SEQ ID NO. 11 | FIP: GGAAGGATGCCATTTTGCCCGGTTAGCTCCCCATTCTGCTC | |
| SEQ ID NO. 12 | BIP: TGAGTGGGCTTGTCGGTAGTCAACACACCAAACTCTGC | |
| SEQ ID NO. 13 | F3: TGACGGTCGATCAATGGTG | *B. bronchiseptica* (Bb) |
| SEQ ID NO. 14 | B3: AGCCAGCTGGAATCATGGA | |
| SEQ ID NO. 15 | FIP: TCGATTCCACGCGCGATCAGTCCCCTGCAGAAAGTACGG | |
| SEQ ID NO. 16 | BIP: GGCATTGAATATTGCCTGGGGCAACATGGTGAAAAGACCCGG | |
| SEQ ID NO. 17 | F3: CGTTGTCAAGGAAGCAGA | *P. multocida* (Pm) |
| SEQ ID NO. 18 | B3: TCCGCTATTTACCCAGTG | |
| SEQ ID NO. 19 | FIP: CGAGCCATAAAATAATGCCATTTCCGTGCGAATGAACCGATTG | |

TABLE 1-continued

Primer sequences in primer sets

| Primer ID | Primer sequence (5'-3') | Pathogenic bacteria |
|---|---|---|
| SEQ ID NO. 20 | BIP: TGAGTGGGCTTGTCGGTAGTCAACACACCAAACTCTGC | |
| SEQ ID NO. 21 | F3: ACACCGATGTCACCAGCA | *S. suis* (SS) |
| SEQ ID NO. 22 | B3: TCGCTTCCACCCAACTGTA | |
| SEQ ID NO. 23 | FIP: TGCGCTTCTGCCAAAGCTTCAGACGTCAAGTGAAGGTCCG | |
| SEQ ID NO. 24 | BIP: CCACCTTTACCACCGCCGATAGTTCCTCGGTTTTGAGCAA | |
| SEQ ID NO. 25 | F3: CGGCTCGAAAATATGATGG | *E. rhusiopathiae* (ER) |
| SEQ ID NO. 26 | B3: GAACATCTCCACTTCTTTGG | |
| SEQ ID NO. 27 | FIP: ACGTTCCAAGTTTGGATATACATCTTCATCCACTGTATCTTGAACT | |
| SEQ ID NO. 28 | BIP: GCGAACGCGGTTGTTGAATCCTGTAGTTTCTTCCCTCTTTGT | |

Example 2

Preparation and Use of LAMP Chip for Detecting Porcine Susceptibility-Related Pathogenic Bacteria 1. Preparation of a LAMP Chip for Detecting Porcine Susceptibility-Related Pathogenic Bacteria In the present disclosure, the microfluidic chip for detecting porcine susceptibility-related pathogenic bacteria included the following components:

(1) Isothermal Amplification Buffer

The isothermal amplification buffer included water as a solvent, and solutes and concentrations thereof were as follows: 1.4 mM dNTPs, a 10× Isothermal Amplification Reaction Buffer, a 100 mM $MgSO_4$ aqueous solution, 10% BSA-A by mass percentage, and SYTO™9. A reaction system of microfluidic LAMP was shown in Table 2.

TABLE 2

Reaction system of microfluidic LAMP

| Component | Volume | Final concentration |
|---|---|---|
| 10× ThermoPol Buffer | 2.5 μL | 1× |
| $MgSO_4$ (100 mM) | 1.5 μL | 6 mM |
| Bst DNA Polymerase Large Fragment | 1 μL | 320 U/mL |
| dNTPMix (10 mM) | 3.5 μL | 1.4 mM |
| 10% BSA-A | 3 μL | |

TABLE 2-continued

| Reaction system of microfluidic LAMP | | |
|---|---|---|
| Component | Volume | Final concentration |
| SYTO™9 | 0.5 μL | |
| Template DNA | 2 μL | |
| SW Water | Making up to 25 μL | |

(2) Isothermal Amplification Enzyme Solution

The isothermal amplification enzyme solution included water as a solvent, and solute and concentration were as follows: Bst DNA Polymerase Large Fragment 320 U/mL.

(3) 32-Well Reaction Cell Disc-Type Microfluidic Chip Loaded with Primer Pairs

The 32-well reaction cell disc-type microfluidic chip was a 4×8 microfluidic chip, produced by Shanghai Igenetec Diagnostics Co., Ltd. A schematic diagram of the microfluidic chip was shown in FIG. 1, In FIG. 1, the reaction cells 7, 15, 23, and 31 in the outer circle were immobilized with the LAMP primers of *A. pleuropneumoniae* provided in Example 1 (SEQ ID NOs: 1 to 4);

the reaction cells 1, 9, 17, and 25 in the outer circle were immobilized with the LAMP primers of *H. parasuis* provided in Example 1 (SEQ ID NOs: 5 to 8);

the reaction cells 2, 10, 18, and 26 marked in the outer circle were immobilized with the LAMP primers of *S. choleraesuis* provided in Example 1 (SEQ ID NOs: 9 to 12);

the reaction cells 3, 11, 19, and 27 in the outer circle were immobilized with the LAMP primers of *B. bronchiseptica* provided in Example 1 (SEQ ID NOs: 13 to 16);

the reaction cells 5, 13, 21, and 29 in the outer circle were immobilized with the LAMP primers of *P. multocida* provided in Example 1 (SEQ ID NOs: 17 to 20);

the reaction cells 6, 14, 22, and 30 in the outer circle were immobilized with the LAMP primers of *S. suis* provided in Example 1 (SEQ ID NOs: 21 to 24);

the reaction cells 7, 15, 23, and 31 in the outer circle were immobilized with the LAMP primers of *E. rhusiopathiae* provided in Example 1 (SEQ ID NOs: 25 to 28); and the reaction cells 8, 16, 24, and 32 were blank controls, with no amplification primers coated.

A method for coating the primers into the disc-type microfluidic chip was as follows: the outer primers and the inner primers corresponding to the pathogenic bacteria were mixed according to a molar ratio of 1:8, and then mixed with trehalose to prepare corresponding mixed solutions. In each mixed solution, the inner primer had a final concentration of 1.6 μM, the outer primer had a final concentration of 0.2 μM, and the trehalose had a mass percentage of 0.5%.

Each mixed solution was added to reaction cells corresponding to the chip, and the LAMP primers were coated into the reaction cells after vacuum heating, compressing, film sealing and stamping; all the LAMP primers of the pathogenic bacteria were coated into the reaction cells of the chip to obtain the LAMP chip for later use.

2. Use of LAMP Chip for Detecting Various Porcine Susceptibility-Related Pathogenic Bacteria (1) Extraction of a Genome A bacterial genome and a non-target bacterial genome were extracted using an extraction kit provided by TIANGEN, to obtain a target bacterial genome and a non-target bacterial genome of the porcine pathogenic bacteria.

The genomic DNA was extracted from clinical samples by the boiling method.

(2) Preparation of a Reaction System

75 μL of the isothermal amplification mixed solution including 3 μL of the isothermal amplification enzyme solution and 6 μL of the target bacterial genome and the non-target bacterial genome of the porcine pathogenic bacteria was mixed evenly by vortex shaking, and injected into the sample hole of the LAMP chip, followed by attaching a parafilm.

(3) Isothermal Amplification and Detection

The LAMP chip was placed in a microfluidic chip detection instrument, centrifuged quickly at 1,500 rpm/min for 15 sec and then 3,500 rpm/min for 30 sec, and reacted at 63° C. for 1 h.

(4) Determination of Results

The results are shown in FIG. 2 to FIG. 8, where corresponding "S" shape in the reaction cell means positive; and flat curve corresponding to the reaction cell means negative.

Figure 2:
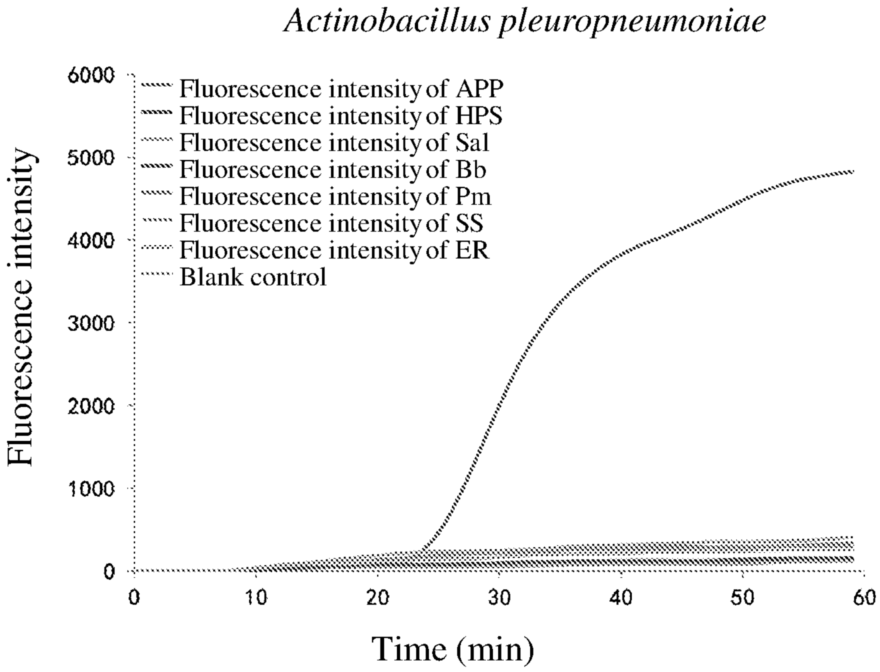
FIG. 2 shows a specificity result of the disc-type microfluidic chip of *A. pleuropneumoniae;*

As can be seen from FIG. 2, the detection results of the reaction cells 7, 15, 23, and 31 of the primer set immobilized with *A. pleuropneumoniae* are "S" shape, showing positive, indicating that the unknown sample is a clinical sample positive for the *A. pleuropneumoniae.*

Figure 3:
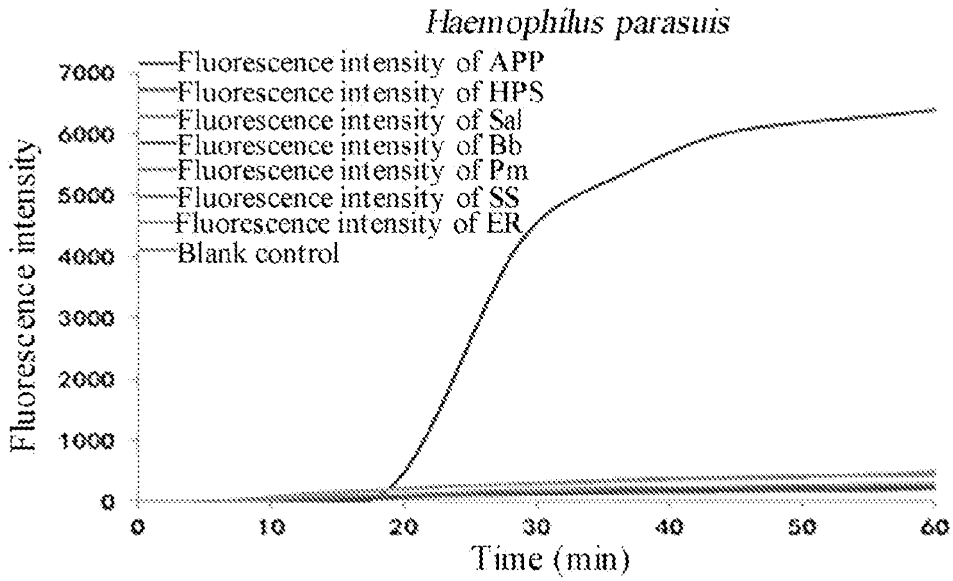
FIG. 3 shows a specificity result of the disc-type microfluidic chip of *H. parasuis;*

As can be seen from FIG. 3, the detection results of the reaction cells 1, 9, 17, and 25 of the primer set immobilized with *H. parasuis* are "S" shape, showing positive, indicating that the unknown sample is a clinical sample positive for the *H. parasuis.*

Figure 4:
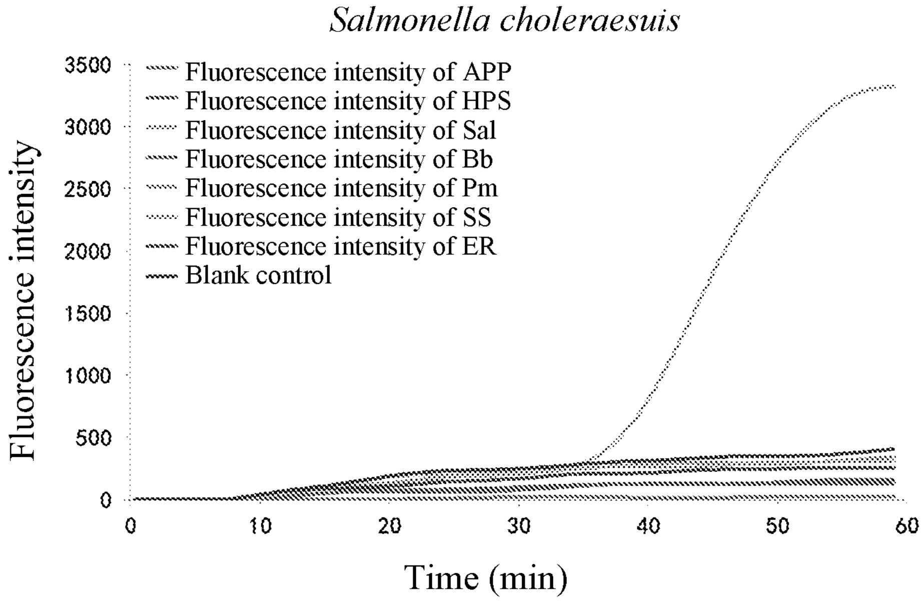
FIG. 4 shows a specificity result of the disc-type microfluidic chip of *S. choleraesuis;*

As can be seen from FIG. 4, the detection results of the reaction cells 2, 10, 18, and 26 of the primer set immobilized with *S. choleraesuis* are "S" shape, showing positive, indicating that the unknown sample is a clinical sample positive for the *S. choleraesuis.*

Figure 5:
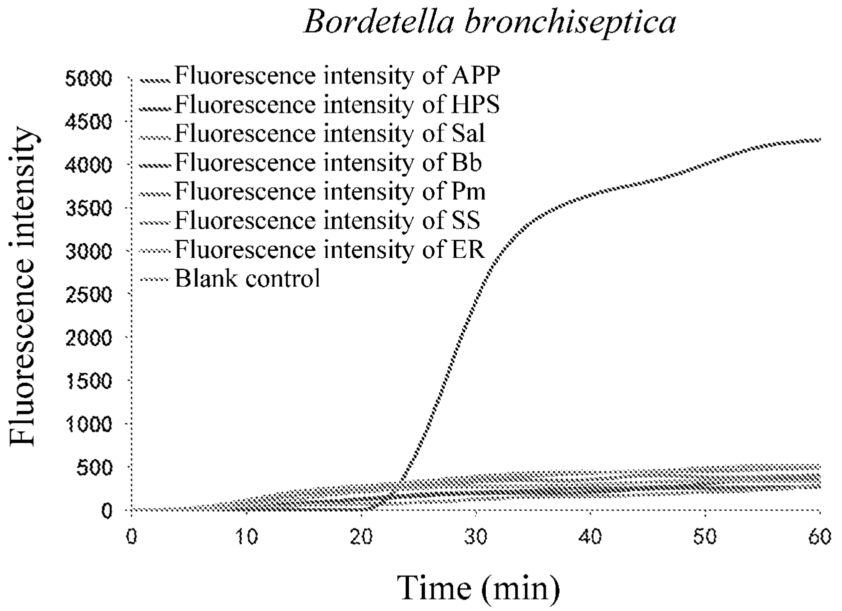
FIG. 5 shows a specificity result of the disc-type microfluidic chip of *B. bronchiseptica;*

As can be seen from FIG. 5, the detection results of the reaction cells 3, 11, 19, and 27 of the primer set immobilized with *B. bronchiseptica* are "S" shape, showing positive, indicating that the unknown sample is a clinical sample positive for the *B. bronchiseptica.*

Figure 6:
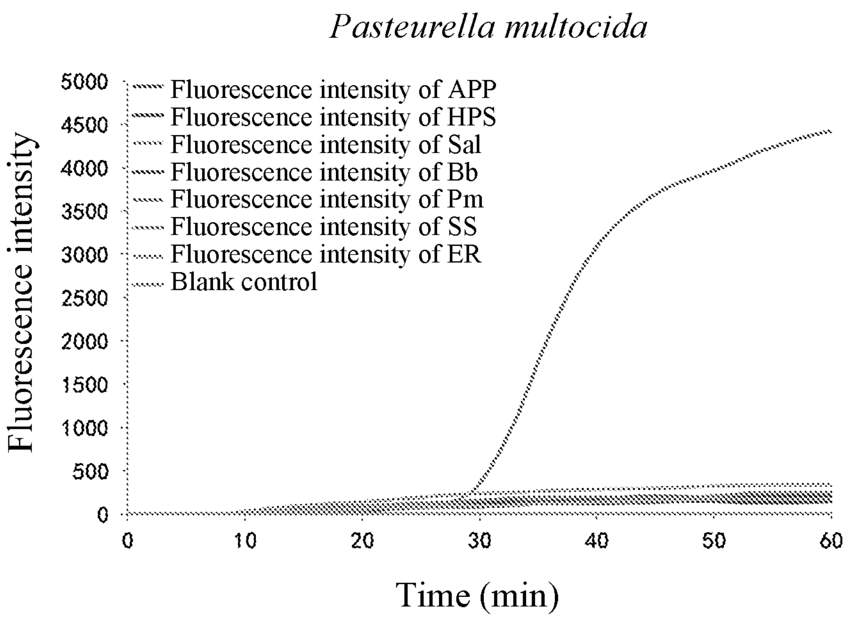
FIG. 6 shows a specificity result of the disc-type microfluidic chip of *P. multocida;*

As can be seen from FIG. 6, the detection results of the reaction cells 5, 13, 21, and 29 of the primer set immobilized with *P. multocida* are "S" shape, showing positive, indicating that the unknown sample is a clinical sample positive for the *P. multocida.*

Figure 7:
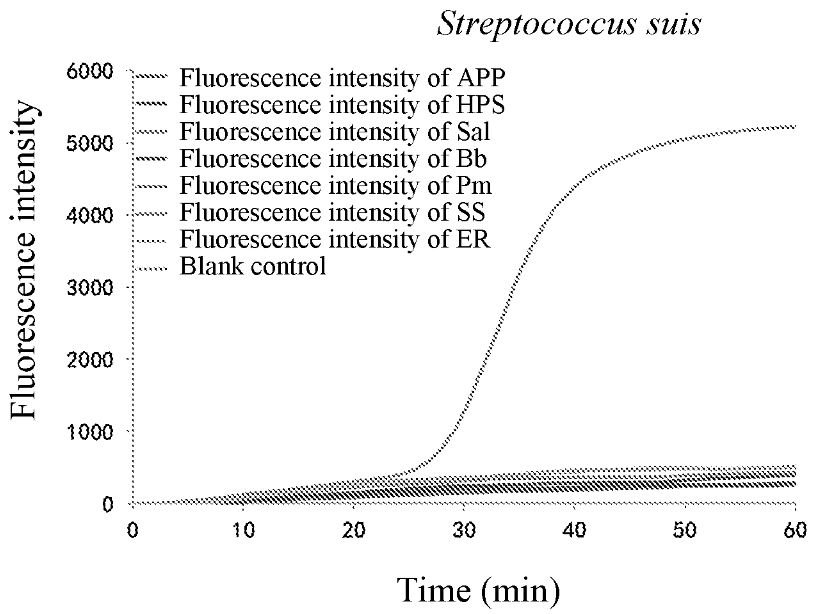
FIG. 7 shows a specificity result of the disc-type microfluidic chip of *S. suis;*

As can be seen from FIG. 7, the detection results of the reaction cells 6, 14, 22, and 30 of the primer set immobilized with *S. suis* are "S" shape, showing positive, indicating that the unknown sample is a clinical sample positive for the *S. suis.*

Figure 8:
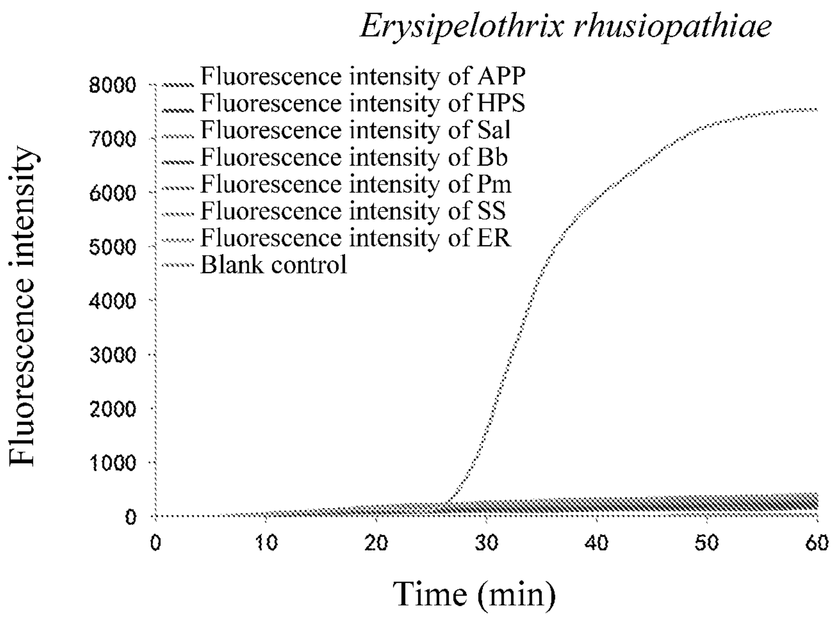
FIG. 8 shows a specificity result of the disc-type microfluidic chip of *E. rhusiopathiae;*
Figure 9:
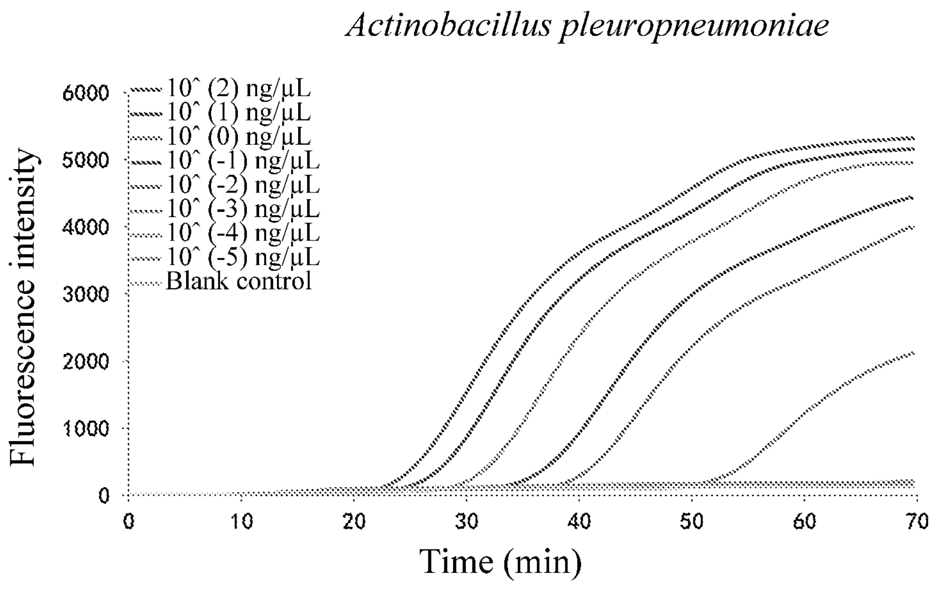
FIG. 9 shows a sensitivity result of the disc-type microfluidic chip of *A. pleuropneumoniae;*
Figure 10:
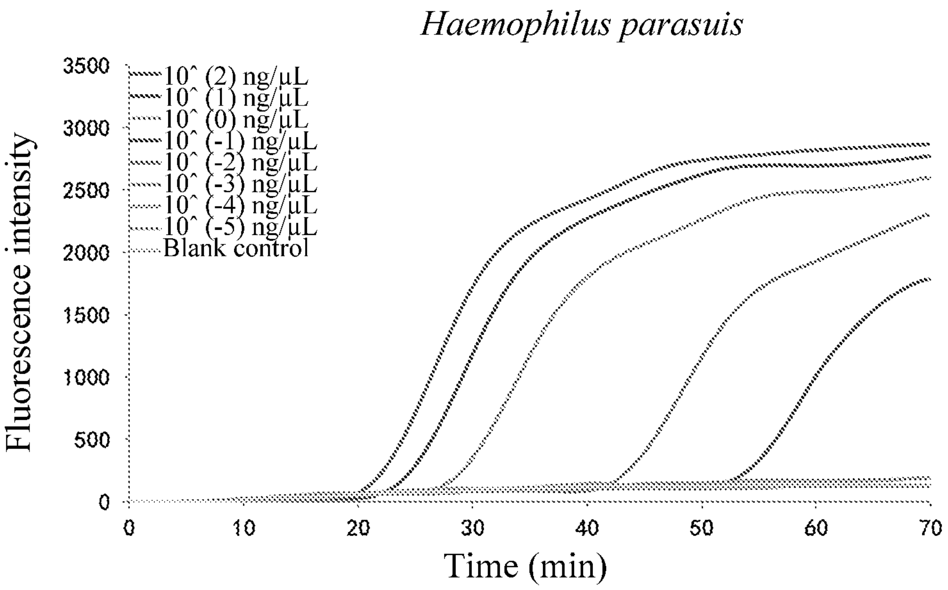
FIG. 10 shows a sensitivity result of the disc-type microfluidic chip of *H. parasuis;*
Figure 11:
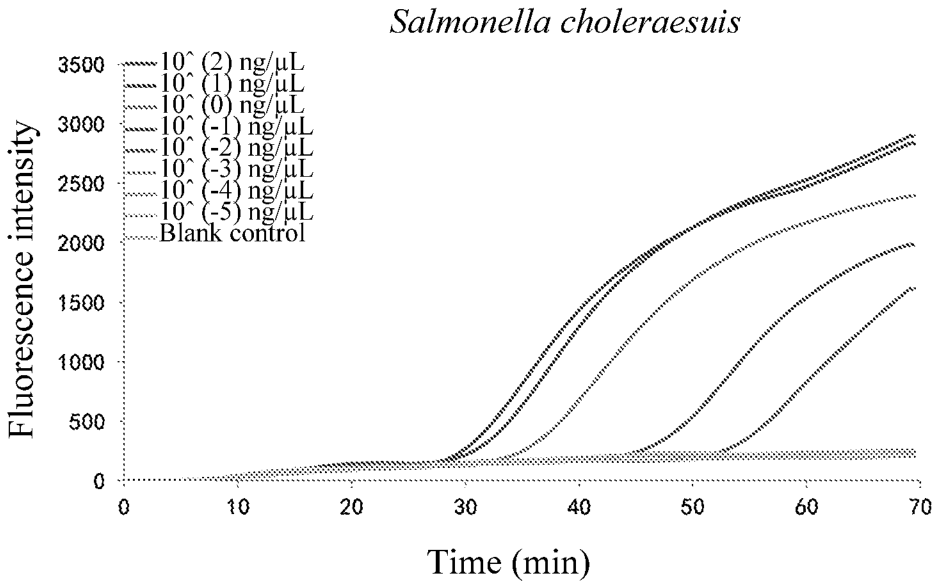
FIG. 11 shows a sensitivity result of the disc-type microfluidic chip of *S. choleraesuis;*
Figure 12:
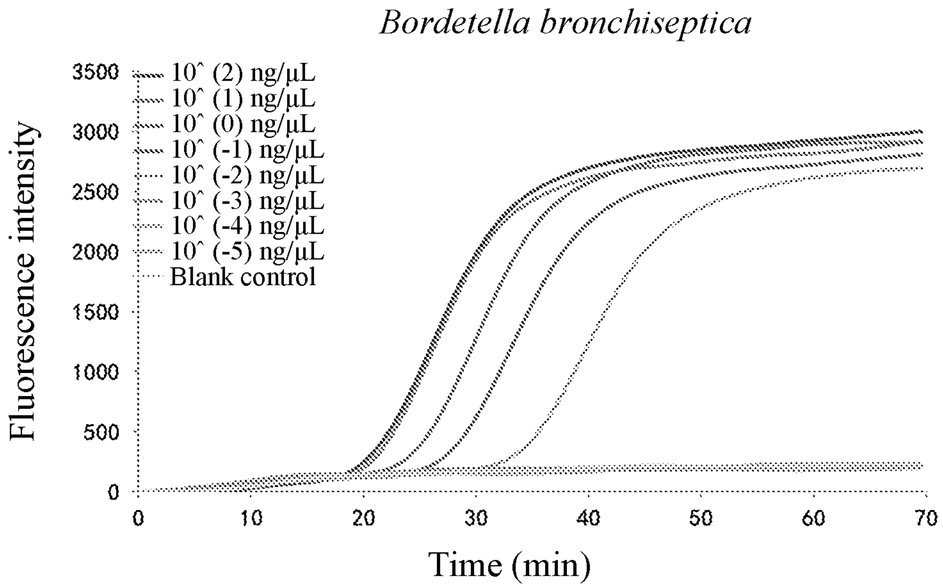
FIG. 12 shows a sensitivity result of the disc-type microfluidic chip of *B. bronchiseptica;*
Figure 13:
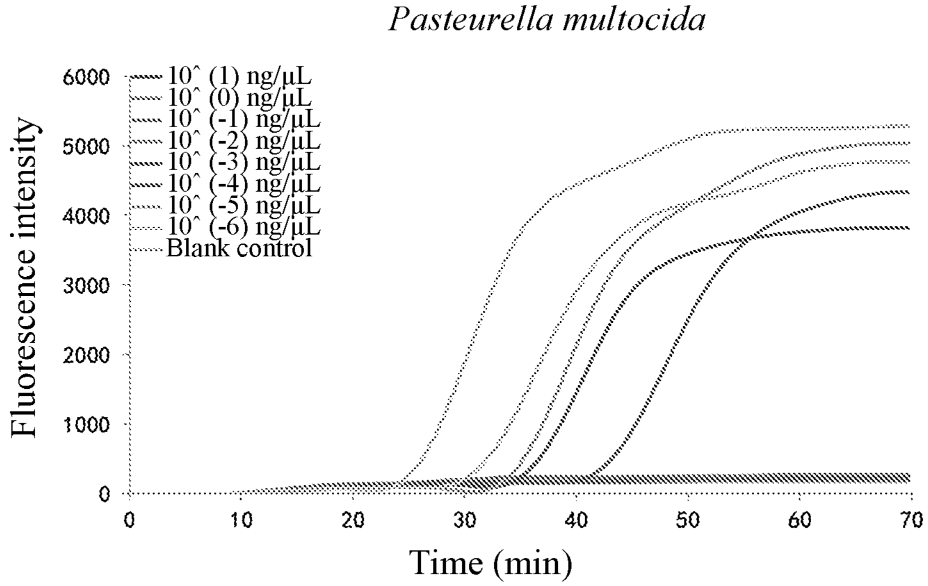
FIG. 13 shows a sensitivity result of the disc-type microfluidic chip of *P. multocida;*
Figure 14:
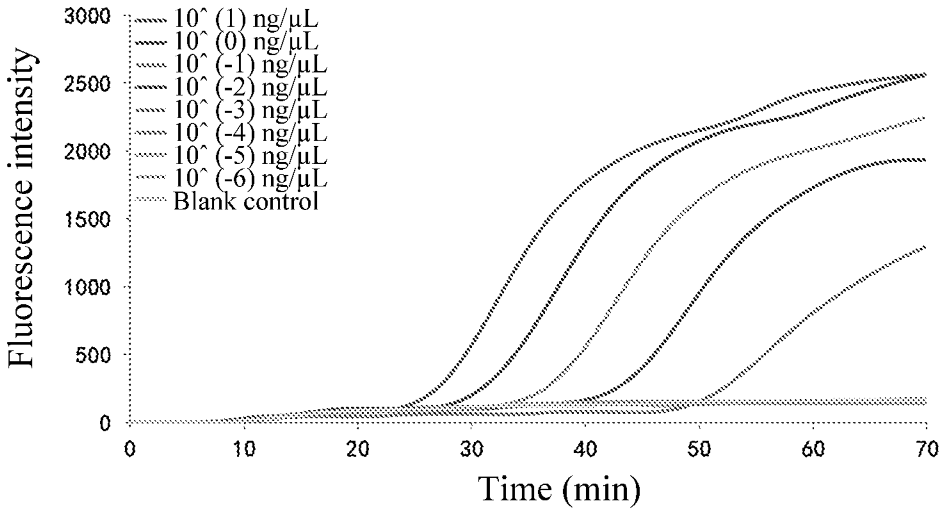
FIG. 14 shows a sensitivity result of the disc-type microfluidic chip of *S. suis*.
Figure 15:
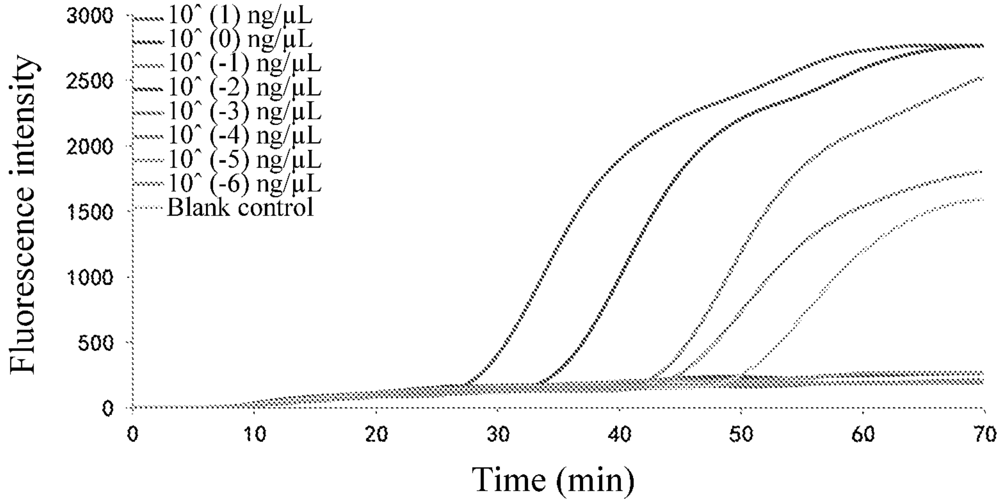
FIG. 15 shows a sensitivity result of the disc-type microfluidic chip of *E. rhusiopathiae.*

As can be seen from FIG. 8, the detection results of the reaction cells 7, 15, 23, and 31 of the primer set immobilized with *E. rhusiopathiae* are "S" shape, showing positive, indicating that the unknown sample is a clinical sample positive for the *E. rhusiopathiae.*

The results show that the LAMP primer sets for detecting porcine susceptibility-related pathogenic bacteria and the LAMP chip based on the same provided by the present disclosure may accurately detect the *A. pleuropneumoniae*, the *H. parasuis*, the *S. choleraesuis*, the *B. bronchiseptica*, the *P. multocida*, the *S. suis*, and the *E. rhusiopathiae.*

The results compared with conventional PCR detection are shown in Table 2.

TABLE 2

| Detection results of clinical samples | | | | | | |
|---|---|---|---|---|---|---|
| | LAMP chip | | Detection | PCR | | Detection |
| Type | Positive | Negative | rate (%) | Positive | Negative | rate (%) |
| *A. pleuropneumoniae* (APP) | 4 | 116 | 3.3 | 4 | 116 | 3.3 |
| *H. parasuis* (HPS) | 1 | 119 | 0.8 | 1 | 119 | 0.8 |
| *S. choleraesuis* (Sal) | 2 | 118 | 1.6 | 2 | 118 | 1.6 |
| *B. bronchiseptica* (Bb) | 1 | 119 | 0.8 | 1 | 119 | 0.8 |
| *P. multocida* (PW) | 4 | 116 | 3.3 | 4 | 116 | 3.3 |
| *S. suis* (SS) | 7 | 113 | 5.8 | 7 | 113 | 5.8 |
| *E. rhusiopathiae* (ER) | 2 | 118 | 1.6 | 2 | 118 | 1.6 |
| Total | 21 | | 17.5 | 21 | | 17.5 |

As can be seen from Table 2, the detection results of the LAMP chip are the same as those of the conventional PCR detection, indicating that the detection method provided by the present disclosure has a detection rate reaching 100%. In addition, the detection method may specifically detect the *A. pleuropneumoniae*, the *H. parasuis*, the *S. choleraesuis*, the *B. bronchiseptica*, the *P. multocida*, the *S. suis*, and the *E. rhusiopathiae*, which has a high specificity and no cross reaction with other pathogens.

Example 3

Sensitivity of LAMP Chip

Sensitivity detection was conducted using the LAMP chip prepared in Example 2.

The nucleic acids of the *A. pleuropneumoniae*, the *H. parasuis*, the *S. choleraesuis*, the *B. bronchiseptica*, the *P. multocida*, the *S. suis*, and the *E. rhusiopathiae* extracted in Example 2 were diluted separately, and then mixed to obtain a mixed nucleic acid.

The *A. pleuropneumoniae* sample had concentration gradients as follows: $1.17\times10^{2}$ ng/μL, $1.17\times10^{1}$ ng/μL, $1.17\times10^{0}$ ng/μL, $1.17\times10^{-1}$ ng/μL, $1.17\times10^{-2}$ ng/μL, $1.17\times10^{-3}$ ng/μL, $1.17\times10^{-4}$ ng/μL, and $1.17\times10^{-5}$ ng/μL.

The *H. parasuis* sample had concentration gradients as follows: $1.27\times10^{2}$ ng/μL, $1.27\times10^{1}$ ng/μL, $1.27\times10^{0}$ ng/μL, $1.27\times10^{-1}$ ng/μL, $1.27\times10^{-2}$ ng/μL, $1.27\times10^{-3}$ ng/μL, $1.27\times10^{-4}$ ng/μL, and $1.27\times10^{-5}$ ng/μL.

The *S. choleraesuis* sample had concentration gradients as follows: $1.57\times10^{2}$ ng/μL, $1.57\times10^{1}$ ng/μL, $1.57\times10^{0}$ ng/μL, $1.57\times10^{-1}$ ng/μL, $1.57\times10^{-2}$ ng/μL, $1.57\times10^{-3}$ ng/μL, $1.57\times10^{-4}$ ng/μL, and $1.57\times10^{-5}$ ng/μL.

The *B. bronchiseptica* sample had concentration gradients as follows: $1.20\times10^{2}$ ng/μL, $1.20\times10^{1}$ ng/μL, $1.20\times10^{0}$ ng/μL, $1.20\times10^{-1}$ ng/μL, $1.20\times10^{-2}$ ng/μL, $1.20\times10^{-3}$ ng/μL, $1.20\times10^{-4}$ ng/μL, and $1.20\times10^{-5}$ ng/μL.

The *P. multocida* sample had concentration gradients as follows: $2.05\times10^{1}$ ng/μL, $2.05\times10^{0}$ ng/μL, $2.05\times10^{-1}$ ng/μL, $2.05\times10^{-2}$ ng/μL, $2.05\times10^{-3}$ ng/μL, $2.05\times10^{-4}$ ng/μL, $2.05\times10^{-5}$ ng/μL, and $2.05\times10^{-6}$ ng/μL.

The *S. suis* sample had concentration gradients as follows: $1.13\times10^{1}$ ng/μL, $1.13\times10^{0}$ ng/μL, $1.13\times10^{-1}$ ng/μL, $1.13\times10^{-2}$ ng/μL, $1.13\times10^{-3}$ ng/μL, $1.13\times10^{-4}$ ng/μL, $1.13\times10^{-5}$ ng/μL, and $1.13\times10^{-6}$ ng/μL.

The *E. rhusiopathiae* sample had concentration gradients as follows: $8.3\times10^{1}$ ng/μL, $8.3\times10^{0}$ ng/μL, $8.3\times10^{-1}$ ng/μL, $8.3\times10^{-2}$ ng/μL, $8.3\times10^{-3}$ ng/μL, $8.3\times10^{-4}$ ng/μL, $8.3\times10^{-5}$ ng/μL, and $8.3\times10^{-6}$ ng/μL.

The mixed nucleic acid was mixed with an isothermal amplification system (namely the isothermal amplification buffer and the isothermal amplification enzyme solution provided in Example 2), and a resulting sample was injected into the isothermal amplification microfluidic chip (namely the LAMP chip prepared in Example 2), and isothermal amplification was conducted at 63° C. for 1 h.

The reaction results are shown in FIG. 9 to FIG. 15, where the *A. pleuropneumoniae* has a minimum limit of detection (LOD) of 1.17 pg/μL; the *H. parasuis* has a minimum LOD of 12.7 pg/μL; the *S. choleraesuis* has a minimum LOD of 15.7 pg/μL; the *B. bronchiseptica* has a minimum LOD of 12.0 pg/μL; the *P. multocida* has a minimum LOD of 2.05 pg/μL; the *S. suis* has a minimum LOD of 1.13 pg/μL; and the *E. rhusiopathiae* has a minimum LOD of 8.3 pg/μL. It showed that the detection method provided by the present disclosure had an extremely high sensitivity.

In the present disclosure, the LAMP chip may accurately detect the *A. pleuropneumoniae*, the *H. parasuis*, the *S. choleraesuis*, the *B. bronchiseptica*, the *P. multocida*, the *S. suis*, and the *E. rhusiopathiae*, thereby making up for the time-consuming and labor-intensive defects of the above pathogen detection technology. The chip may also expand a detection range of pathogens, improve a detection sensitivity and specificity, reduce labor intensity, and shorten a detection cycle. The detection method may also visually determine the detection results with naked eyes without expensive PCR detection instruments, making this method fast, simple, and easy to popularize, safe and reliable in scientific research and production practice, and suitable for field operation. For clinical purposes, the detection of porcine susceptibility-related pathogenic bacteria can be conducted within 1 h, and the detection results are not only faster than the commonly-used PCR methods, but also of great significance for rapid auxiliary guidance of treatment and medication. In addition, the multi-indicator typing detection may also be used for epidemiological investigation and epidemic monitoring.

The present disclosure has been disclosed with preferred examples as above, which shall not be construed as a limitation to the present disclosure. Any person skilled in the art can make changes and variations without departing from the spirit and scope of the present disclosure. The protection scope of the present disclosure shall be defined by the claims.

SEQUENCE LISTING INFORMATION

DTD Version: V1_3
File Name: HLP20220602422-sequence listing.xml
Software Name: WIPO Sequence
Software Version: 2.0.0
Production Date: 2022 Jul. 26
General Information:
Current application/Applicant file reference: HLP20220602422
Earliest priority application/IP Office: CN
Earliest priority application/Application number: 202110965791.1
Earliest priority application/Filing date: 2021 Aug. 23
Applicant name: Anhui Agricultural University
Applicant name/Language: en
Invention title: LOOP-MEDIATED ISOTHERMAL AMPLIFICATION (LAMP) PRIMER SETS FOR DETECTING PORCINE SUSCEPTIBILITY-RELATED PATHOGENIC BACTERIA, AND KIT, LAMP CHIP AND USE BASED ON THE SAME (en)
Sequence Total Quantity: 35
Sequences:
Sequence Number (ID): 1
Length: 19
Molecule Type: DNA
Features Location/Qualifiers:
source, 1 . . . 19
>mol_type, other DNA
>note, Forward outer primer for *Actinobacillus pleuropneumoniae*
>organism, synthetic construct
Residues:
cccttagccc cttacacta 19
Sequence Number (ID): 2
Length: 18
Molecule Type: DNA
Features Location/Qualifiers:
source, 1 . . . 18
>mol_type, other DNA
>note, Reverse outer primer for *Actinobacillus pleuropneumoniae*
>organism, synthetic construct
Residues:
cgcttaggat ccgcctta 19
Sequence Number (ID): 3
Length: 40
Molecule Type: DNA
Features Location/Qualifiers:
source, 1 . . . 40
>mol_type, other DNA
>note, Forward inner primer for *Actinobacillus pleuropneumoniae*
>organism, synthetic construct
Residues:
caccaccgag aaacaaatcc tcggcgtggt ttatgtcacc 40
Sequence Number (ID): 4
Length: 45
Molecule Type: DNA
Features Location/Qualifiers:
source, 1 . . . 45
>mol_type, other DNA
>note, Reverse inner primer for *Actinobacillus pleuropneumoniae*
>organism, synthetic construct
Residues:
aggcgataca attgaagacg ccggtacccc tttttctctc accac 45

Sequence Number (ID): 5
Length: 18
Molecule Type: DNA
Features Location/Qualifiers:
source, 1 . . . 18
>mol_type, other DNA
>note, Forward outer primer for *Haemophilus parasuis*
>organism, synthetic construct
Residues:
acctactttt acgcctcc 18
Sequence Number (ID): 6
Length: 18
Molecule Type: DNA
source, 1 . . . 18
>mol_type, other DNA
>note, Reverse outer primer for *Haemophilus parasuis*
>organism, synthetic construct
Residues:
gcattggtca agctggtt 18
Sequence Number (ID): 7
Length: 41
Molecule Type: DNA
Features Location/Qualifiers:
source, 1 . . . 41
>mol_type, other DNA
>note, Forward inner primer for *Haemophilus parasuis*
>organism, synthetic construct
Residues:
caggcattga aggtttgacg tttatcatca cgctcatttg c 41
Sequence Number (ID): 8
Length: 46
Molecule Type: DNA
source, 1 . . . 46
>mol_type, other DNA
>note, Reverse inner primer for *Haemophilus parasuis*
>organism, synthetic construct
Residues:
accttttttg tttgtgttgt ttgctaaagt ataggtgttg gtactg 46
Sequence Number (ID): 9
Length: 23
Molecule Type: DNA
Features Location/Qualifiers:
source, 1 . . . 23
>mol_type, other DNA
>note, Forward outer primer for *Salmonella choleraesuis*
>organism, synthetic construct
Residues:
cattgccaag tatctgtatc agc 23
Sequence Number (ID): 10
Length: 20
Molecule Type: DNA
Features Location/Qualifiers:
source, 1 . . . 20
>mol_type, other DNA
>note, Reverse outer primer for *Salmonella choleraesuis*
>organism, synthetic construct
Residues:
ccggatgcac taaggcttta 20
Sequence Number (ID): 11
Length: 41
Molecule Type: DNA Features Location/Qualifiers:
source, 1 . . . 41
>mol_type, other DNA
>note, Forward inner primer for *Salmonella choleraesuis*
>organism, synthetic construct
Residues:
ggaaggatgc cattttgccc ggttagetcc ccattctgct c 41
Sequence Number (ID): 12
Length: 38
Molecule Type: DNA
Features Location/Qualifiers:
source, 1 . . . 38
>mol_type, other DNA
>note, Reverse inner primer for *Salmonella choleraesuis*
>organism, synthetic construct
Residues:
tgagtgggct tgtcggtagt caacacacca aactctgc 38
Sequence Number (ID): 13
Length: 19
Molecule Type: DNA
Features Location/Qualifiers:
source, 1 . . . 19
>mol_type, other DNA
>note, Forward outer primer for *Bordetella bronchiseptica*
>organism, synthetic construct
Residues:
tgacggtcga tcaatggtg 19
Sequence Number (ID): 14
Length: 19
Molecule Type: DNA
Features Location/Qualifiers:
source, 1 . . . 19
>mol_type, other DNA
>note, Reverse outer primer for *Bordetella bronchiseptica*
>organism, synthetic construct
Residues:
aatcatgga agccagctgg 19
Sequence Number (ID): 15
Length: 39
Molecule Type: DNA
source, 1 . . . 39
>mol_type, other DNA
>note, Forward inner primer for *Bordetella bronchiseptica*
>organism, synthetic construct
Residues:
tcgattccac gcgcgatcag tcccctgcag aaagtacgg 39
Sequence Number (ID): 16
Length: 42
Molecule Type: DNA
Features Location/Qualifiers:
source, 1 . . . 42
>mol_type, other DNA
>note, Reverse inner primer for *Bordetella bronchiseptica*
>organism, synthetic construct
Residues:
ggcattgaat attgcctggg gcaacatggt gaaaagaccc gg 42
Sequence Number (ID): 17
Length: 18
Molecule Type: DNA
source, 1 . . . 18
>mol_type, other DNA
>note, Forward outer primer for *Pasteurella multocida*
>organism, synthetic construct
Residues:
cgttgtcaag gaagcaga 18
Sequence Number (ID): 18
Length: 18
Molecule Type: DNA
Features Location/Qualifiers:
source, 1 . . . 18
>mol_type, other DNA
>note, Reverse outer primer for *Pasteurella multocida*
>organism, synthetic construct
Residues:
tccgctattt acccagtg 18
Sequence Number (ID): 19
Length: 43
Molecule Type: DNA
Features Location/Qualifiers:
source, 1 . . . 43
>mol_type, other DNA
>note, Forward inner primer for *Pasteurella multocida*
>organism, synthetic construct
Residues:
cgagccataa aataatgcca tttccgtgcg aatgaaccga ttg 43
Sequence Number (ID): 20
Length: 38
Molecule Type: DNA
Features Location/Qualifiers:
source, 1 . . . 38
>mol_type, other DNA
>note, Reverse inner primer for *Pasteurella multocida*
>organism, synthetic construct
Residues:
tgagtgggct tgtcggtagt caacacacca aactctgc 38
Sequence Number (ID): 21
Length: 18
Molecule Type: DNA
Features Location/Qualifiers:
source, 1 . . . 18
>mol_type, other DNA
>note, Forward outer primer for *Streptococcus suis*
>organism, synthetic construct
Residues:
acaccgatgt caccagca 18
Sequence Number (ID): 22
Length: 19
Molecule Type: DNA
source, 1 . . . 19
>mol_type, other DNA
>note, Reverse outer primer for *Streptococcus suis*
>organism, synthetic construct
Residues:
tcgcttccac ccaactgta 19
Sequence Number (ID): 23
Length: 40
Molecule Type: DNA
Features Location/Qualifiers:
source, 1 . . . 40
>mol_type, other DNA
>note, Forward inner primer for *Streptococcus suis*
>organism, synthetic construct
Residues:
tgcgcttctg ccaaagcttc agacgtcaag tgaaggtccg 40

Sequence Number (ID): 24
Length: 40
Molecule Type: DNA
source, 1 . . . 40
>mol_type, other DNA
>note, Reverse inner primer for *Streptococcus suis*
>organism, synthetic construct
Residues:
ccacctttac caccgccgat agttcctegg ttttgagcaa 40
Sequence Number (ID): 25
Length: 19
Molecule Type: DNA
Features Location/Qualifiers:
source, 1 . . . 19
>mol_type, other DNA
>note, Forward outer primer for *Erysipelothrix rhusiopathiae*
>organism, synthetic construct
Residues:
cggctcgaaa atatgatgg 19
Sequence Number (ID): 26
Length: 20
Molecule Type: DNA
Features Location/Qualifiers:
source, 1 . . . 20
>mol_type, other DNA
>note, Reverse outer primer for *Erysipelothrix rhusiopathiae*
>organism, synthetic construct
Residues:
gaacatctcc acttctttgg 20
Sequence Number (ID): 27
Length: 46
Molecule Type: DNA
Features Location/Qualifiers:
source, 1 . . . 46
>mol_type, other DNA
>note, Forward inner primer for *Erysipelothrix rhusiopathiae*
>organism, synthetic construct
Residues:
acgttccaag tttggatata catcttcatc cactgtatct tgaact 46
Sequence Number (ID): 28
Length: 42
Molecule Type: DNA
Features Location/Qualifiers:
source, 1 . . . 42
>mol_type, other DNA
>note, Reverse inner primer for *Erysipelothrix rhusiopathiae*
>organism, synthetic construct
Residues:
gcgaacgcgg ttgttgaatc ctgtagtttc ttccctcttt gt 42
Sequence Number (ID): 29
Length: 652
Molecule Type: DNA
Features Location/Qualifiers:
source, 1 . . . 652
>mol_type, other DNA
>note, DNA sequence of the APX IV gene
>organism, synthetic construct
Residues:
ccggcaacga cagtaagatt gaaggcacta aaatcacccg taggattgg ggtaaagaag 60 ttacgcttga tattgccaat cagaaaattg aaaaaggcgt gtcagagaaa ttggggctgt 120
ctgttagtgg ttcg-gatatc attaaattgt tgtttggagc attgactcca actttaaata 180
gaatgttgct atcacaacte atccagtctt tttccgatag cttggctaaa cttgataatc 240
ccttagcccc ttacactaaa aatggcgtgg tttatgt-cac cggcaaaggg aatgatgtgc 300
ttaaaggaac tgaacatgag gatttgtttc tcggtggtga ggggaatgat acttattatg 360
cgagagtagg cgatacaatt taaagtctat tttgtgagag gaagacgccg acggcaaagg 420
ataacgaaag aaaaaggggt acctaaggcg gatcctaagc gggtagagtt tagcgagtac 480
aattataatt aaggggttat taacctacgc agttttagaa agaggttgaa aagaaataaa 540
gggaagagaa aacggcgact ttcgctcatg cgactatgct taat-gagctt tttactgatt 600 atactaatta tcgttatgaa gttaaaggac taaaattgcc cgccgttaaa aa 652
Sequence Number (ID): 30
Length: 605
Molecule Type: DNA
source, 1 . . . 605
>mol_type, other DNA
>note, DNA sequence of the OMP P2 gene
>organism, synthetic construct
Residues:
tettgegcca gttcttacga agtcaatttt ctctttaaca ttacctgttt ttt-caacacc 60 atgaccacca tcaacageta cagtaaatgg agcat-tgaca tatttaagac caaagtatac 120
accatctttg tetttcttat taacagatce agatttatag tcatcatgag tataacctgc 180 tatt-tagcac ctaaaccaaa tgccacagtt acagattgac tttccgcaat cttagctgtg 240
gccagattta gcagaaccta cttttacgcc tccct-tatca tcacgctcat ttgcaacatt 300
atagttagca cctaacgtca aaccttcaat gcctgtatag gtatagttaa ttgctgaatc 360 agaatct-gaa gtaaggatat caaaaccttt tttgtttgtg ttgtttgctg aatatttaat 420
tccaccagta ccaacaccgt atactttatc aaaaccagct tgac-caatgc tatcaccgat 480 tacagcttgt ttaccaaaag aaatttcatg accatagcca cctaaaccga cgtaagcata 540
ttttgtttta acatcgcccc atcctgcage atttttagaa ttactgtcaa ggogagtctc 600 ataac 605
Sequence Number (ID): 31
Length: 407
Molecule Type: DNA
Features Location/Qualifiers:
source, 1 . . . 407
>mol_type, other DNA
>note, DNA sequence of the invA gene
>organism, synthetic construct
Residues:
atgcaacatt togatatcgc tgaattagtt cgttccgcac tggaagtaag tggttgcgat 60
ccttcactca teggaggaat agatagccat tcaacaattg ttctggattt atttgcattg 120
ccaagtatct gtatcagegt caaggacgat gatgtatgga tctgggcgca attgggtgct 180
gacagcatgg tggtattaca acagegggct tatgaaatct taatgaccat aatggaagga 240
tgccattttg cccgcggegg gcaattacta ctgggggagc agaatgggga gctaacgctt 300
aaagccttag tgcatccgga ttttttatct gacggtgaaa agttctctac tgccttgaat 360
gggttttaca actatctgga agtttttagt cggtcgctaa tgagatg 407
Sequence Number (ID): 32
Length: 547
Molecule Type: DNA
Features Location/Qualifiers:
source, 1 . . . 547
>mol_type, other DNA
>note, DNA sequence of the DNT gene
>organism, synthetic construct
Residues:
atcgcgggcg tgctctgcga tctcgagagc gegcagcgca cgttgcccgt cgtattggcc 60
aggtttcggc cccttggcgt gcttgcgcga ttcagaaggc tggagcagga aaccgcgggc 120
atgctgcttg gcgaccagga gccggagcct cggggcttca tcagttttac cgattttcgc 180
gatagcgacg cgttcgccag ctacgcggag tatgcggccc agttcaacga ctatatcgat 240
caatacagca tactcgaggc gcagcggctg gcgcggattc tggccctggg ctcgcggatg 300
acggtcgatc aatggtgcct tcccctgcag aaagtacggc actacaaggt gctgacatcg 360
cagccaggge tgatcgcgcg tggaatcgaa aatcacaaca ggggcattga atattgcctg 420
gggcggccgc cgctgaccga tctgccgggt cttttcacca tgttccagct ccatgattcc 480
agctggctgt tggtatcgaa catcaacggt gagctttggt ctgatgtcct tgcgaacgct 540
gaggtga 547

Sequence Number (ID): 33
Length: 457
Molecule Type: DNA
Features Location/Qualifiers:
source, 1 . . . 457
>mol_type, other DNA
>note, DNA sequence of the kmt1 gene
>organism, synthetic construct
Residues:
gctgtaaacg aactcgccac tttttgtttc atttggactg acacgatcaa accgttgaac 60
acgaagaaaa agaccaaaat aggtaaccaa tacacgataa ataaattaaa ccgctctgcc 120
gttaatggct tcaataatgg ccataagaaa cgtaactcaa catggaaata ttgataaatc 180
agactgacaa aacaataagc tgagtaataa ataacgtcca ggaaatataa accggcaaat 240
atcagttgcg ccgttgtcaa ggaagcagat tggctcaaca caccaaactc cgcccaacaa 300
aactgtgctt ttctttgcca cacgccaaat aaaagactac cgacaagccc actcacaacg 360
aactcaattt cgcggcaatc agtggcataa agccataaaa taatgccatt tcccatttca 420
ggttcattcg caccgcccca ctgggtaaat agcggat 457

Sequence Number (ID): 34
Length: 689
Molecule Type: DNA
source, 1 . . . 689
>mol_type, other DNA
>note, DNA sequence of the gdh gene
>organism, synthetic construct
Residues:
gcagcgtatt ctgtcaaacg agcgcggcgt ttttctttga tgtccaccaa gaggtcgaag 60
tcgataccag tttegtcaat gatgtaacca tttgagtctg aaacagaaat aacttttgca 120
ccaagttcag tcgctttttg aacagcatat tgggcaacgt taccagaacc tgagataagg 180
acagtttggt ctttgaagga tttaccgttt gctgccaaca tgttatcagt gaagtaaacc 240
tgggoggatc aatgaaccac cgaagccaag aggtttacca aaaccgtaac cagttgcttc 300
gtaaccgatc gtcaagacac ctgcatcaaa ctggcggagg cgtttgtatt gaccgtacat 360
tcacgaccac cgacaccgat gtcaccagca gggacgtcaa gtgaaggtcc gatgtgtttt 420
tgcaattcag tcatgaagct ttggcagaag cgcatgattt cagcatcagt ttttccttta 540
gaccagtcaa gacgtttttg ggatcaaagt ctgaaccacc tttaccaccg ccgattggaa 600
aagatttgct caaaaccgag gaacttcaag atggattggt ttacagttgg gtggaagcga 600
agaccgcctt tataaggacc tacagctgag ttgaactgaa cacggtagcc acggttgact 660
tgaacatttc catctttatc tgtccatgg 689

Sequence Number (ID): 35
Length: 1881
Molecule Type: DNA
source, 1 . . . 1881
>mol_type, other DNA
>note, DNA sequence of the spaA gene
>organism, synthetic construct
Residues:
atgaaaaaga acttttaaca aaaaacacct atttccgaaa gtaagtctta tgtcgtgctt 60
gcaatgccac tacaaacage ttttgctgat tcgacagata tttctgtgat tccactaatc 120
ggtgaacaag ttggattgct cccagtttta cctgggacag gggtacatgc tcaggaatac 180
aacaaaatga ctgatgctta tattgaaaaa ttggtatctc taattaatca aaaagtgaag 240
ccgtttctta taaatgaacc aaagggggtac caaagtttcg aagcagtgaa tgaagagatt 300
taagtgaact taaaaatgaa ggaatgagtc ttcaaaacat tcaccatatg aactcgattg 360
cctagcaact agaatcggct acagaagttt tatgcaggat tttaaacaaa gcatccaaaa 420
aacttgatga agcatacgtt gctatgtatc ttgaaaattt tgaaagatta acgattcctg 480
gatttactcg tgaattacga ggtgaaacac cgtattttag taaaatatga aggtaaagtt 540
togtagtatg aaaggtagag ctcccttaga agcatttata gttcctctaa gagatagaat 600
aatgaaattg ctgcagaagt aaattattta cctgaagcgc atgaggattt cttagtttca 660
gattcaagcg agtataatga caaactaaat aatatcaact ttgctttggg tctaggggtc 720
agcgagttta ttgactataa ccggctcgaa aatatgatgg aaaaagaact tcatccactg 780
tatcttgaac tttatgctat gcggagaaat cgccaaattc aagttgtaag agatgtatat 840
ccaaacttgg aacgtgcgaa cgcggttgtt gaatccttaa agacaattaa agatataaaa 900
caaagaggga agaaactaca ggaacttett gaaatttata tccaaagaag tggagatgtt 960
cgaaaaccag atgtactcca acgatttatt ggaaaatatc aatcagtagt tgatgaagaa 1020
aaaaataaac ttcaagatta tttagaatca gatatttttg attcatatag tgtg-gatggc 1080
gaaataaaga aattacactc atcaatagag atgcatactt atctatgatt gagaaaataa 1140
tacagagctc aatcgatttc ggaaattaag acgattcgtg cagatttaga atcacttgtc 1200
aaatcattcc aaaatgaaga aagtgactct aaagtagagc ctgaaagtcc cgttaaagta 1260
gatcaaaaga agctagttga tcaatcaaaa gaaaaaccag ttgatgaaga aaaacctaaa 1320
attcaaaaga agggtggatt aagaaagata ataagtggtt ctatattgag cccgaatcga 1380
aaatcaggtg gaatggcaac aggttggaag aaggtagcag acaaatggta ctacctcgat 1440
aatacgggtg ctatagttac gggttggaag aaggtagcaa acaaatggta ctatcttgaa 1500
aaatcaggtg cgatggcaac aggatggaag aaagtatcaa acaagtggta ctaccttgaa 1560
aactcaggtg caatggcaac aggatggaag aaagtatcaa acaagtggta ctaccttgaa 1620
aattcaggcg caatggctac aggatggaaa aaggtagcaa acaaatggta ctaccttgaa 1680
aactcaggtg cgatggcaac aggatggaag aaagtatcga acaagtggta ctaccttgaa 1740
aactcaggcg caatggctac aggatggaaa aaggtagcaa acaaatggta ctaccttgat 1800
tctattgatg gtaaaaagta tgcatttaag aaatcaggaa tgatggttac aggttcaaag 1860
aacgatggaa gtttaaaata g 1881

What is claimed is:

1. Loop-mediated isothermal amplification (LAMP) primer sets for detecting porcine susceptibility-related pathogenic bacteria, wherein the porcine susceptibility-related pathogenic bacteria comprise: *Actinobacillus pleuropneumoniae, Haemophilus parasuis, Salmonella choleraesuis, Bordetella bronchiseptica, Pasteurella multocida, Streptococcus suis*, and *Erysipelothrix rhusiopathiae*; and the LAMP primer sets comprise an *Actinobacillus pleuropneumoniae* primer set, an *H. parasuis* primer set, an *S. choleraesuis* primer set, a *B. bronchiseptica* primer set, a *P. multocida* primer set, an *S. suis* primer set, and an *E. rhusiopathiae* primer set;

the *Actinobacillus pleuropneumoniae* primer set comprises a forward outer primer F3 with the nucleotide sequence set forth in SEQ ID NO: 1, a reverse outer primer B3 with the nucleotide sequence set forth in SEQ ID NO: 2, a forward inner primer FIP with the nucleotide sequence set forth in SEQ ID NO: 3, and a reverse inner primer BIP with the nucleotide sequence set forth in SEQ ID NO: 4;

the *H. parasuis* primer set comprises a forward outer primer F3 with the nucleotide sequence set forth in SEQ ID NO: 5, a reverse outer primer B3 with the nucleotide sequence set forth in SEQ ID NO: 6, a forward inner primer FIP with the nucleotide sequence set forth in SEQ ID NO: 7, and a reverse inner primer BIP with the nucleotide sequence set forth in SEQ ID NO: 8;

the *S. choleraesuis* primer set comprises a forward outer primer F3 with the nucleotide sequence set forth in SEQ ID NO: 9, a reverse outer primer B3 with the nucleotide sequence set forth in SEQ ID NO: 10, a forward inner primer FIP with the nucleotide sequence set forth in SEQ ID NO: 11, and a reverse inner primer BIP with the nucleotide sequence set forth in SEQ ID NO: 12;

the *B. bronchiseptica* primer set comprises a forward outer primer F3 with the nucleotide sequence set forth in SEQ ID NO: 13, a reverse outer primer B3 with the nucleotide sequence set forth in SEQ ID NO: 14, a forward inner primer FIP with the nucleotide sequence set forth in SEQ ID NO: 15, and a reverse inner primer BIP with the nucleotide sequence set forth in SEQ ID NO: 16;

the *P. multocida* primer set comprises a forward outer primer F3 with the nucleotide sequence set forth in SEQ ID NO: 17, a reverse outer primer B3 with the nucleotide sequence set forth in SEQ ID NO: 18, a forward inner primer FIP with the nucleotide sequence set forth in SEQ ID NO: 19, and a reverse inner primer BIP with the nucleotide sequence set forth in SEQ ID NO: 20;

the *S. suis* primer set comprises a forward outer primer F3 with the nucleotide sequence set forth in SEQ ID NO: 21, a reverse outer primer B3 with the nucleotide sequence set forth in SEQ ID NO: 22, a forward inner primer FIP with the nucleotide sequence set forth in SEQ ID NO: 23, and a reverse inner primer BIP with the nucleotide sequence set forth in SEQ ID NO: 24; and the *E. rhusiopathiae* primer set comprises a forward outer primer F3 with the nucleotide sequence set forth in SEQ ID NO: 25, a reverse outer primer B3 with the nucleotide sequence set forth in SEQ ID NO: 26, a forward inner primer FIP with the nucleotide sequence set forth in SEQ ID NO: 27, and a reverse inner primer BIP with the nucleotide sequence set forth in SEQ ID NO: 28.

2. A kit of porcine susceptibility-related pathogenic bacteria, comprising the LAMP primer sets according to claim 1 and a reaction buffer.

3. The kit according to claim 2, wherein the reaction buffer comprises Bst DNA Polymerase, a 10× Isothermal Amplification Reaction Buffer, BSA-A, dNTP, an $MgSO_4$ aqueous solution, and a fluorescent dye.

4. A LAMP chip for detecting porcine susceptibility-related pathogenic bacteria, comprising the LAMP primer sets according to claim 1, a reaction buffer, and a chip.

5. The LAMP chip according to claim 4, wherein in the LAMP primer sets, an outer primer pair and an inner primer pair corresponding to any one of the pathogenic bacteria have a molar ratio of 1:8.

6. The LAMP chip according to claim 4, wherein the reaction buffer comprises Bst DNA Polymerase, a 10× Isothermal Amplification Reaction Buffer, BSA-A, dNTP, an $MgSO_4$ aqueous solution, and a fluorescent dye.

7. The LAMP chip according to claim 4, wherein the chip comprises an isothermal amplification microfluidic chip.

8. The LAMP chip according to claim 4, wherein an amplification reaction cell of the LAMP chip comprises: an *H. parasuis* reaction cell, an *S. choleraesuis* reaction cell, a *B. bronchiseptica* reaction cell, a *P. multocida* reaction cell, an *S. suis* reaction cell, an *E. rhusiopathiae* reaction cell, an *Actinobacillus pleuropneumoniae* reaction cell, and a negative control reaction cell.

* * * * *